United States Patent
Combs et al.

[11] Patent Number: 5,868,682
[45] Date of Patent: Feb. 9, 1999

[54] DEVICE AND PROCESS FOR GENERATING AND MEASURING THE SHAPE OF AN ACOUSTIC REFLECTANCE CURVE OF AN EAR

[75] Inventors: Jerome T. Combs, Wallingford; Hugh W. Busey, Cheshire; Kresimir Ukraincik, Cromwell, all of Conn.

[73] Assignee: MDI Instruments, Inc., Woburn, Mass.

[21] Appl. No.: 878,174

[22] Filed: Jun. 18, 1997

Related U.S. Application Data

[63] Continuation of Ser. No. 592,655, Jan. 26, 1996, Pat. No. 5,699,809, which is a continuation of Ser. No. 378,504, Jan. 26, 1995, abandoned, Ser. No. 378,654, Jan. 26, 1995, abandoned, and Ser. No. 560,523, Nov. 17, 1995, abandoned, which is a continuation of Ser. No. 378,503, Jan. 26, 1995, abandoned.

[51] Int. Cl.[6] .................................................... A61B 5/00
[52] U.S. Cl. ................................................................ 600/559
[58] Field of Search ..................................... 600/559, 561; 73/585

[56] References Cited

U.S. PATENT DOCUMENTS

| | | |
|---|---|---|
| D. 286,814 | 11/1986 | Brainard, II et al. . |
| 3,294,193 | 12/1966 | Zwislocki . |
| 3,395,697 | 8/1968 | Mendelson . |
| 3,757,769 | 9/1973 | Arguimbau ................... 128/2 |
| 3,882,848 | 5/1975 | Klar ............................ 128/2 |
| 3,949,735 | 4/1976 | Klar et al. . |
| 4,002,161 | 1/1977 | Klar et al. . |
| 4,009,707 | 3/1977 | Ward ........................... 128/2 |
| 4,057,051 | 11/1977 | Kerouac . |
| 4,079,198 | 3/1978 | Bennett . |
| 4,201,225 | 5/1980 | Bethea, III et al. ........ 128/746 |
| 4,237,905 | 12/1980 | Keller ....................... 128/746 |
| 4,251,686 | 2/1981 | Sokolich ...................... 179/1 |
| 4,289,143 | 9/1981 | Canavesio et al. . |
| 4,326,416 | 4/1982 | Fredberg ..................... 73/597 |
| 4,374,526 | 2/1983 | Kemp . |
| 4,378,809 | 4/1983 | Cosman ..................... 128/748 |
| 4,586,194 | 4/1986 | Kohashi et al. ............... 381/60 |
| 4,596,252 | 6/1986 | Nelson .................... 128/419 PG |
| 4,601,295 | 7/1986 | Teele ........................ 128/746 |
| 4,615,007 | 9/1986 | King et al. . |

(List continued on next page.)

FOREIGN PATENT DOCUMENTS

| | | |
|---|---|---|
| WO/79/ 000614 | 6/1979 | WIPO . |

OTHER PUBLICATIONS

Ahroon et al.; "The Role of Tuning Curve Variables and Threshold Measures in the Estimation of Sensory Cell Loss" Audiology 1993, 32; pp. 244–259.

(List continued on next page.)

Primary Examiner—Max Hindenburg
Attorney, Agent, or Firm—Wolf, Greenfield & Sacks, P.C.

[57] ABSTRACT

A device and a process for analysis of an ear directs into the ear acoustic waves Measurements may be made without pressurizing the ear canal and contact between the device and the ear does not need to be air-tight. The patient experiences essentially no discomfort from use of the device. The device detects the reflected waves to produce what is called an acoustic reflectance curve. The shape of a region of the acoustic reflectance curve is electronically measured in order to obtain an indicator of ear condition which is substantially independent of a line of sight between a sound source and the ear. This indicator may be based on a measurement of the resonance characteristic, or freedom of motion, of the tympanic membrane or other ear component being analyzed. One such measurement is the rate of change of the acoustic reflectance with respect to frequency. The rate of change measured around the null may be presented as an angle measurement, a gradient or slope measurement, a width measurement, or other form of measurement of the shape of the null. The steepest slopes on either side of a null may be used to define an angle. Diagnosis of an ear pathology, such as abnormal pressure or presence of fluid in the middle ear or conductive hearing loss, may be based on this measure alone.

15 Claims, 19 Drawing Sheets

U.S. PATENT DOCUMENTS

| | | |
|---|---|---|
| 4,674,123 | 6/1987 | Michas ..................................... 381/60 |
| 4,677,679 | 6/1987 | Killion ..................................... 381/74 |
| 4,688,582 | 8/1987 | Heller et al. . |
| 4,748,598 | 5/1988 | Kopke . |
| 4,754,748 | 7/1988 | Antowski .................................. 128/40 |
| 4,763,753 | 8/1988 | Killion .................................... 181/130 |
| 4,809,708 | 3/1989 | Geisler et al. ........................... 128/746 |
| 4,813,430 | 3/1989 | Hecox et al. ............................ 128/746 |
| 4,819,753 | 4/1989 | Higo et al. ............................... 128/773 |
| 4,841,986 | 6/1989 | Marchbanks ............................ 128/746 |
| 4,884,447 | 12/1989 | Kemp et al. . |
| 4,966,160 | 10/1990 | Birck et al. .............................. 128/746 |
| 5,063,946 | 11/1991 | Wada ....................................... 128/746 |
| 5,105,822 | 4/1992 | Stevens et al. . |
| 5,179,079 | 1/1993 | Hansen et al. .............................. 514/4 |
| 5,230,344 | 7/1993 | Özdamar et al. . |
| 5,267,571 | 12/1993 | Zurek et al. . |
| 5,316,002 | 5/1994 | Jackson et al. ..................... 128/602.06 |
| 5,348,002 | 9/1994 | Caro ........................................ 128/633 |
| 5,372,142 | 12/1994 | Madsen et al. .......................... 128/739 |
| 5,402,493 | 3/1995 | Goldstein ................................ 128/746 |
| 5,413,114 | 5/1995 | Zurek et al. . |
| 5,421,818 | 6/1995 | Arenberg ................................... 604/21 |
| 5,445,144 | 8/1995 | Wodicka et al. ................. 128/207.144 |
| 5,526,819 | 6/1996 | Lonsbury-Martin et al. .......... 128/773 |
| 5,594,174 | 1/1997 | Keefe ........................................ 73/585 |
| 5,601,091 | 2/1997 | Dolphin .................................. 128/746 |
| 5,651,371 | 7/1997 | Keefe ...................................... 128/746 |
| 5,666,960 | 9/1997 | Fredberg et al. ........................ 128/716 |
| 5,699,809 | 12/1997 | Combs et al. ........................... 128/746 |

OTHER PUBLICATIONS

Buhrer et al.; "The Acoustic Reflectometer as a Screening Device: A Comparison"; Ear and Hearing 1995; vol. 6, No. 6 pp. 307–314.

Schwartz et al.; "Validity of Acoustic Reflectometry in Detecting Middle Ear Effusion"; Pediatrics vol. 79, No. 5; May, 1987 pp. 739–742.

Combs, JT; "Effect of Tip Size on Acoustic Reflectometry"; The Pediatric Infectious Disease Journal vol. 11, No. 11, 1992; pp. 978–979.

Gates et al.; "Efficacy of Acoustic Reflectometry in Detecting Middle Ear Effusion"; Ann. Otal. Rhinol; 95;1986 pp. 472–476.

Wall et al.; "Reliability and Performance of the Acoustic Reflectometer"; The Journal of Family Practice. vol. 23, No. 5 1986; pp. 443–447.

Combs, J.T.; "Observations on the Calibration of Acoustic Reflectometry" Brief Reports: The Pediatric Infectious Disease Journal; vol 7, No. 9; Sep. 1988; pp. 659–660.

Boswell et al.; "Reflectometric Screening for Otitis Media: Inconsistencies in a Sample of Australian Aboriginal Children" International Journal of Pediatric Otorinolaryngology, vol. 25; pp. 49–60; 1993.

Shera et al; "Noninvasive Measurement of the Cochlear Traveling–Wave Ratio" J. Acoust. Sco. Am. 93 (6) pp. 3333–3352; Jun. 1993.

Harwin et al.; "Acoustic Relectometry and Hearing Loss in Acute Otitus Media" General Pediatrics and Pediatric Education; vol. 143A; No. 843, 1993.

Douniadakis et al.; "Evaluation of Acoustic Reflectometry in Detecting Otitus Media in Children" British Journal of Audiology; vol. 27, pp. 409–414; 1993.

Buczko, "Principal Respects of Development of the Acoustic Impedance Meter," Medicor News, No. 1, 1978, pp. 39–45.

Combs, J.T., "Change of Acoustic Reflectivity With Age," Journal of Pediatrics, vol. 117, pp. 80–82, Jul. 1990.

Combs, J.T., "Single vs. Double Acoustic Reflectometry Tracings," Ped. Infect. Dis. J., Sep. 1989, vol. 8, p. 616ff.

Compagnone, A., et al., "Reducing False Positive Results in Screening for Middle Ear Effusion," The Hearing Journal, Aug. 1988, vol. 41, p. 14ff.

DeCicco, Michael, "Hear, Hear — A Device to Revolutionize the Industry," Southeastern Massachusetts Business Digest. Sep. 1990, pp. 31–34.

ENT Medical Devices, "Recent Advances in Micro–Electronics Make the New Acoustic Otoscope More Versatile and Even Easier to Use," Appln Note T–7, 1991).

ENT Medical Devices, "A Simple Pain–Free Way to Confirm Middle Ear Effusion Even in Crying or Fussing Children," Flyer, 1991).

ENT Medical Devices, "Acoustic Otoscope and Sonar Impedance Analyzer," Operating Instructions, 1990.

ENT Medical Devices, "When Typmanometry Isn't Enough," Application note 502, published Sep. 1984.

Harwin, Jonathan, "Acoustic Reflectometry and Hearing Loss in Pediatric Patents With Acute Otitis Media," Thesis, Yale Medical School, 1993.

Jehle, D. and Cottington, E., "Acoustic Otoscopy in the Diagnosis of Otitis Media," Ann. Emerg. Med., Apr. 1989, 18:396–400.

Johnson, Doris, "Wareham Firm Diagnoses Ear Problems With Sonar," Mass. High Tech., Mar. 13–26, 1989, p. 24.

Lonsbury–Martin, Brenda et al., "The Clinical Potential of Otoacoustic–Emissions Testing," Tex. J. of Audiology and Speech Pathology, vol. SV, No. 2, Fall/Winter 1989, pp. 3–9.

Lucae A. Uber eine neue Methode zur Untersuchung des Gehororgans zu physiologischen und diagnostischen Zwecken mit Hulfe des Interferenz–Otoscopes, Arch Ohren 1967;3:86–194. (German).

Macknin, M.L., et al., "Acoustic Reflectometry Detection of Middle Ear Effusion," Pediatric Infectious Disease Journal, 1987; 6:866–868.

Market Intelligence Research Corp., "Medical Equipment Markets for Eye, Ear, Nose and Throat Applications: Niche Opportunities Prevail," 1986), Section VII, pp. VII–1 to VII–3.

Modena et al., "A New Artificial Ear for Telephone Use," J. Acoustic. Soc. Am., vol. 63, No. 5, pp. 1604–1610. 1978.

Otodynamics, Ltd., Advertisement. The Hearing Journal, vol. 45, No. 11, Nov. 1992, p. 20.

Oyiborhoro, J.M., et al. "Efficacy of Acoustic Otoscope in Detecting Middle Ear Effusion in Children," Laryngoscope, Apr. 1987; 97;495–498.

Pichichero, M.E., et al., "Anatomic and Audiologic Sequelae After Tympanostomy Tube Insertion," Pediatric Infectious Disease Journal, Nov. 1989, pp. 780–786.

Pinto and Dallos, "An Acoustic Bridge for Measuring the Static and Dynamic Impedance of the Eardrum," IEEE Transactions on Bio–Medical Engineering, vol. PME–15, No. 1, Jan. 1968, pp. 10–16.

Schwartz, R., "Managing Otitis Media," Pediatric Management, Oct. 1990, pp. 20–28.

Sohn, Bernard, et al., "Acoustic Reflectometry: A New Tool for Hearing Screening," 1991.

Stinson, M.R., et al., "Estimation of Acoustical Energy Reflectance at the Eardrum From Measurements of Pressure Distribution in the Human Ear Canal," J. Acoust. Soc. Ann., vol. 72, No. 3, Sep. 1982, pp. 766–773.

Zwislocki, J., "Analysis of Middle–Ear Function, Part I: Input Impedance," Journal of the Acoust. Soc. of America, vol. 34, No. 8, Part 2, pp. 1514–1523, Sep. 1962.

"Early Warning Test for Otitis Media," Advertisement, Pediatric Management, dated prior to 1993.

"Device Can Test for Loss of Hearing in Infants," Pediatric News, Jan. 1991, p. 34.

"64 December New Products," Bay State Business World, Feb. 16, 1983, p. 4.

Teele, David W. et al., Use of a Teaching Pneumatic Otoscope, JAMA, Dec. 14, 1979, vol. 242, No. 24, p. 2664.

Brooks, Lee J. et al., Reproducibility of Measurements of Upper Airway Area by Acoustic Reflection, The American Physiological Society, 1989, p. 2901.

Brooks, Lee J. et al., Relationship Between Lung Volume and Tracheal Area as Assessed by Acoustic Reflection, the American Physiological Society, 1988, p. 1050.

Hilberg, O. et al., Acoustic Rhinometry; Evaluation of Nasal Cavity Geometry by Acoustic Reflection, the American Physiological Society, 1989, p. 295.

Bambonis, LTC Thomas R., et al., Impedance Typanometry and Acoustic Reflectometry at Myringotomy, Pediatrics, vol. 87, No. 4, Apr. 1991, pp. 475–480.

Blood, I., et al., Acoustic Otoscopic Measures in Toddler Population, Poster Presentation American Speech Language Hearing Association, Seattle, WA (Nov. 1990).

Combs, Jerome T., M.D. The Diagnosis of Otitis Media; New Techniques, Pediatric Infectious Disease Journal, vol. 13, No. 11, 1994, pp. 1039–1046.

Combs, J., Predictive Value of the Angle of Acoustic Reflectometry, in the Pediatric Infectious Disease Journal, 1991, vol. 10, No. 3 (Mar.) pp. 214–216.

Combs, Jerome T., Precision of Acoustic Reflectometry with Recorder in Acute Otitis Media, Pediatric Infectious Disease Journal, vol. 7. No. 5, 1988, pp. 329–330.

Combs, Jerome T., Two Useful Tools for Exploring the Middle Ear, Contemporary Pediatrics, Nov. 1993, pp. 60–75.

Endeco Medical, Inc., New Acoustic Otoscope Effective, ENT & Allergy Today, May 1985.

Endeco Medical, Inc., Testing for Middle Ear Fluid— It's A Whole Lot Faster, And A Lot More Fun, Than It Used To Be, Advertisement for "Acoustic Otoscope", 1995.

ENT Medical Devices, Early Detection of Middle Ear Disease, 1992 ENT Medical Devices, Inc..

ENT Medical Devices, Inc., Isn't It Curious That Most Physicians Who Buy A Sonar Ear Analyzer Have Already Tried Tympanometry?, Advertisement for the Sonar Ear Analyzer, dated prior to (1995).

Howie, Virgil M., M.D., Otitis Media, Pediatrics in Review, vol. 4, No. 8, Aug. 1993, pp. 320–323.

Lampe, Col. Richard M., et al., Acoustic Reflectometry in the Detection of Middle Ear Effusion, Pediatrics, vol. 76, No. 1, Jul. 1985, pp. 75–78.

Lampe, Richard H., M.D., Diagnostic Value of Acoustic Reflectometry in Children With Acute Otitis Media, Pediatric Infectious Disease Journal, vol. 8, No. 1, Jan. 1989, pp. 59–61.

Teele, David W. et al., Acoustic Reflectometry for Assessment of Hearing Loss in Children With Middle Ear Effusion, Pediatric Infectious Disease Journal, 1990, vol. 9, pp. 870–872.

Teele, David W. et al., Detection of Middle Ear Effusion by Acoustic Reflectometry, The Journal of Pediatrics, vol. 104, No. 6, Jun. 1984, pp. 832–838.

Lai, Vincent W.S. et al., The Objective Assessment of Nasal Patency; ENT Journal, Jun. 1993, vol. 72, No. 6, 4 pages.

E. Benson Laboratories, Inc., Eccovision and Acoustic Rhinometry System; Aug. 1993, 8.

Combs, Jerome T. et al., Listen to the Ear; New Generation of Acoustic Geometry, pp. 1–6 and references.

Combs, Jerome T. et al., Acoustic Reflectometry; Spectral Analysis and the Conductive Hearing Loss of Otitis Media, The Pediatric Infectious Disease Journal, vol. 15, No. 9, 1996, pp. 683–686.

Keefe, Douglas H. et al., Ear–Canal Impedance and Reflection Coefficient in Human Infants and Adults, J. Acoust. Soc. Am., vol. 94, No. 5, Nov. 1993, pp. 2617–2638.

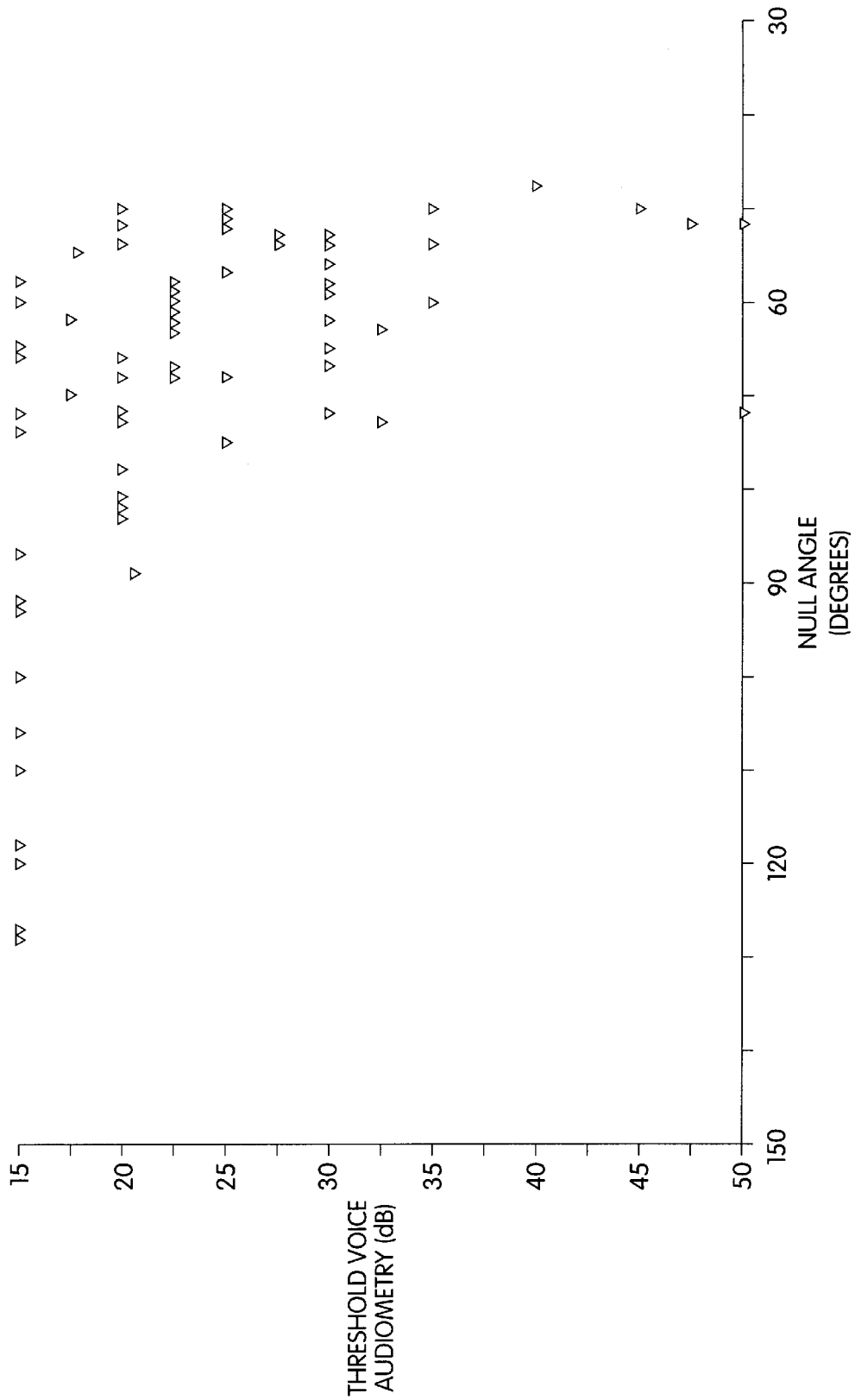

| SPREAD IN NULL VALUES (REFLECTIVITY) | AVERAGE RATIO |
|---|---|
| 50% OR MORE | 3.8 |
| 30% OR MORE | 2.7 |
| 20% OR MORE | 2.5 |
| 10% OR MORE | 2.1 |
| ALL | 1.8 |

Fig. 19

DEVICE AND PROCESS FOR GENERATING AND MEASURING THE SHAPE OF AN ACOUSTIC REFLECTANCE CURVE OF AN EAR

CROSS-REFERENCE TO RELATED APPLICATIONS

This application is a continuation of patent application Ser. No. 08/592,655, filed Jan. 26, 1996, entitled A DEVICE AND PROCESS FOR GENERATING AND MEASURING THE SHAPE OF AN ACOUSTIC REFLECTANCE CURVE OF AN EAR and now U.S. Pat. No. 5,699,809, which is a continuing application claiming the benefit under 35 U.S.C. §120 of U.S. patent application Ser. No. 08/378,504, filed Jan. 26, 1995, now abandoned, and U.S. patent application Ser. No. 08/378,654, filed Jan. 26, 1995, now abandoned and U.S. patent application Ser. No. 08/560,523, filed Nov. 17, 1995, now abandoned and which is a file wrapper continuation application of U.S. patent application Ser. No. 08/378,503, filed Jan. 26, 1995, now abandoned.

FIELD OF THE INVENTION

The present invention relates generally to devices and processes which provide information about a condition of an ear for use in diagnosis of ear pathologies. More particularly, the invention relates to devices and processes which involve measuring acoustic reflectance of components of the ear.

BACKGROUND OF THE INVENTION

A wide variety of diseases associated with the human and animal ears have been identified. The more frequently diagnosed pathologies include obstruction of the external ear canal, atresia of the external ear canal, perforation of the tympanic membrane, retraction of the tympanic membrane, otitis in its various forms (adhesive, purulent and non-purulent), otosclerosis, fixation of the stapes, and cholesteatoma, among others. In children, otitis media is one of the most common pathologies. By itself, otitis media is a significant affliction which can lead to serious long-term hearing and learning disabilities if not promptly diagnosed and treated. Further, otitis media is frequently symptomatic of other pathologies, and thus useful in their diagnosis.

These ear pathologies are generally diagnosed using common diagnostic techniques, such as tympanometry, pneumatic otoscopy or visual otoscopy. While the usefulness of these techniques is well-recognized and established, these techniques do have some difficulties. For example, with both tympanometry and otoscopy, personnel who conduct tests and interpret results must be highly trained. Since these techniques cannot be performed by non-medical or inexperienced personnel, efficient screening of children or infants at home or in a school is not possible with these techniques.

Additionally, a patient must cooperate with the personnel performing these techniques, but patients subjected to these techniques may experience considerable discomfort. In particular, discomfort from tympanometry or pneumatic otoscopy arises since (1) an airtight seal is required to obtain useful measurements, (2) any probe assembly must be inserted deep into the ear canal, and (3) the air pressure in the ear canal must be varied above and below atmospheric pressure to obtain useful measurements.

The diagnosis of otitis media in young children using common diagnostic techniques is particularly difficult because of the fear, discomfort or even pain, associated with many of these techniques. The usefulness of examination by conventional techniques is often diminished because discomfort of the child typically leads, at best, to movement by the child which impairs the examination and, at worst, to a refusal to allow the examination to proceed. The problem is especially acute when the examination is made in a mass screening environment, such as may take place in hospital clinics where large numbers of patients must be seen in a comparatively short time.

Many of the problems with these common diagnostic techniques were overcome by a device which measures acoustic reflectance, which is a quantity related to the complex acoustic impedance of the middle ear. A suitable device and methodology for measuring acoustic reflectance are disclosed and described in U.S. Pat. Nos. 4,601,295 and 4,459,966 to John H. Teele (the Teele patents). Such devices were made commercially available by ENT Medical Devices, Inc., of Wareham, Mass., and Endeco, Inc., of Marion, Mass. In the literature, this diagnostic technique is generally referred to as acoustic reflectometry and the device is generally referred to as an acoustic reflectometer or acoustic otoscope.

Acoustic reflectometry involves transmitting sound waves (called incident waves) through the ear canal to the tympanic membrane. Some of the incident waves are reflected off the tympanic membrane and other components of the ear. The incident waves are selected from a range of frequencies including the resonance frequency of the tympanic membrane; ideally the amplitudes of the incident waves are also the same but this is often not achievable. The vector sum of these reflected waves with the incident waves is obtained by a microphone. The envelope of the vector sum of the incident and reflected waves over the range of frequencies, herein called an acoustic reflectance curve, has a dip, also called a null. The peak of this dip, actually a minimum, is known as a null value. In the literature and in its commercial use, acoustic reflectometers calculate an acoustic reflectance curve for an ear and detect the presence and frequency centerline of the dip and the null value. The null value is the primary basis for diagnosis of ear pathologies. Although the Teele patents state that "shape" of the characteristic dip can be detected along with the presence, frequency and amplitude of the dip, these patents do not discuss significance of the shape of the characteristic dip other than that shape means how pronounced or sharp the dip is. The Teele patents do not discuss how shape of the dip is detected or measured or how it is used in diagnosis.

One of the commercially available acoustic reflectometers was a "T"-shaped device which provided the amplitude of the null value and the incident frequency at which it occurred using a set of horizontal diodes to indicate the frequency at which a dip occurred, and a set of vertical diodes to indicate the null value. This device, the Model 501 Acoustic Otoscope from ENT Medical Devices, Inc., could be equipped with a recorder, or printer, that allowed a visual representation of the entire acoustic reflectance curve to be viewed.

Several articles in the literature describe how the null value of an acoustic reflectance curve obtained using commercially available devices is correlated with ear pathologies. In particular, severe middle ear effusion (MEE) generally causes high null values, whereas normal ears cause low null values. However, there is a significant range of measurements for which the diagnosis is uncertain, e.g., probable MEE such as when an effusion is just beginning to develop. Such a range of uncertainty limits the sensitivity and specificity of the process and device. The literature also includes several studies which reach a variety of conclusions on the specificity and sensitivity of the device for diagnosing MEE.

It was discovered that the accuracy of the measurement of the null value obtained with an acoustic reflectometer depended on the line of sight from the instrument tip to the tympanic membrane. A direct line of sight provides the most accurate results. When a direct line of sight is not obtained, due to improper aiming or because of the ear itself, measurements of the null value are less likely to indicate an unhealthy ear and are more likely to fall in the range of uncertainty, indicating only probable MEE. An unhealthy ear may be diagnosed as healthy.

Due to this range of uncertainty, commercially available acoustic otoscopes were eventually provided with operating instructions that directed a user to look at the overall shape of the dip, when the acoustic otoscope was used with a recorder or printer. It was stated that, given detection of a null value in the uncertain range, a somewhat rounded dip suggests a dry ear condition or negative pressure behind the tympanic membrane but no effusion. It was further states that a sharply peaked dip suggests a condition where the middle ear is partly air-filled, partly fluid-filled.

These operating instructions were based primarily on a study by Jerome T. Combs, entitled, "Predictive value of the angle of acoustic reflectometry," in The Pediatric Infectious Disease Journal, vol. 10, no. 3, pp. 214–216, March 1991. This article states that an "angle" formed at the null of the acoustic reflectance curve, as displayed on the Model 501 Acoustic Otoscope with recorder, is useful in combination with the null value to distinguish healthy ears from unhealthy ears where the null value is inconclusive. Angle measurements were performed manually on the printout using a protractor or goniometer. The paper does not describe any controlled procedure by which points or lines on the printed acoustic reflectance curve were selected to define the angles being manually measured.

The article describes a study in which acoustic reflectance measurements were obtained for 406 ears of 203 children (96 girls and 107 boys) between the ages of 4 and 16 using the Model 501 Acoustic Otoscope with recorder. Of this number, there were 75 ears of tympanometry, 149 ears of tympanometry and 182 ears of tympanometry. The purpose of the study was to determine whether the "angle" formed by the dip in the acoustic reflectance curve had any predictive value. Although the article does conclude that "angle" apparently has some predictive value, there are two problems with the study that suggest that the results lack adequate statistical significance to be conclusive about this predictive value. First, the number of subjects analyzed was arbitrarily selected. This actual number of subjects is statistically insignificant. A much greater sample would be more statistically persuasive. Second, the angle formed by the dip was measured manually using a protractor on a printout of the acoustic reflectance curve. Since the paper lacks a description of a deterministic method for establishing the points defining the angle, the angle measurements are likely to have a fair amount of a variance in them, further weakening the statistical significance of the results.

While an acoustic reflectometer is a useful diagnostic tool, there remain some unsolved problems in achieving accurate diagnoses. First, inexperienced personnel are more likely to obtain inaccurate results because accurate measurement of the null value of acoustic reflectance still requires a direct line of sight from the tip of the acoustic reflectometer to the tympanic membrane. Second, the ears of young children reflect less of the incident waves than those of older children, given the same ear pathology. In particular, children under six months of age have a tympanic membrane which is at a relatively shallow angle to the ear canal. In some cases, this position of the tympanic membrane prevents a direct line of sight from being obtained. These two factors may result in a measurement of the null value in a "healthy" range for an unhealthy ear.

SUMMARY OF THE INVENTION

This invention is related to a device and a process for analysis of acoustic reflectance of components of an ear. In the invention, the shape of a region of an acoustic reflectance curve is electronically measured in order to obtain an indicator of ear condition which is substantially independent of a line of sight between a sound source and the tympanic membrane. This indicator is based on a measurement of the resonance characteristic, or freedom of motion, of the tympanic membrane or other ear component being analyzed. One such measurement is the rate of change of the acoustic reflectance with respect to frequency. Since resonance typically causes a null to appear in the acoustic reflectance curve, this measurement of the rate of change is particularly informative if measured around the null. The rate of change measured around the null may be presented as an angle measurement, a gradient or slope measurement, a width measurement, or other form of measurement of the shape of the null. In one embodiment, the steepest slopes on either side of a null are used to define an angle, herein called a spectral gradient. Diagnosis of an ear pathology, such as abnormal pressure or presence of fluid in the middle ear or such as conductive hearing loss, may be based on this measure alone.

Because of the rate of change of an acoustic reflectance measurement is relatively constant for a given ear, regardless of the quality of the line of sight to the tympanic membrane, the effect, if any, of user training on such measurements is significantly reduced over the prior art. Accordingly, the process and device of the invention are useful in many kinds of diagnostic situations with respect to ear pathology, but particularly in those involving screening of the ears of young children for common pathologies such as Otitis Media, even by untrained personnel.

Accordingly, one aspect of the present invention is a device for analyzing acoustic reflectance of an ear having a tympanic membrane. This device measures acoustic reflectance of components of the ear for a plurality of frequencies by directing sound from a sound source to the tympanic membrane and by detecting reflected sound, wherein the measured acoustic reflectance has a shape. The shape of a region of the measured acoustic reflectance is electronically measured to obtain an indicator of a condition of the ear, wherein the indicator is substantially independent of a line of sight from the sound source to the tympanic membrane.

Another aspect of the invention is a device for analyzing acoustic reflectance of an ear having a tympanic membrane. This device includes an acoustic reflectance measurement system which directs sound of a plurality of frequencies to the tympanic membrane and which detects sound reflected by components of the ear to provide a measure of acoustic reflectance having a shape. A signal shape analyzer has an input connected to receive the measured acoustic reflectance and an output providing an indicator of a condition of the ear, wherein the indicator is substantially independent of a line of sight from the sound source to the tympanic membrane.

Another aspect of the invention is a process for analyzing acoustic reflectance of an ear having a tympanic membrane. The process involves measuring acoustic reflectance of components of the ear for a plurality of frequencies by directing sound from a sound source to the tympanic membrane and by detecting reflected sound, wherein the measured acoustic reflectance has a shape. The shape of the measured acoustic reflectance is electronically measured to obtain an indicator of a condition of the ear, wherein the indicator is substantially independent of a line of sight from the sound source to the tympanic membrane.

In one embodiment of the invention, the indicator is a measure of the rate of change of the acoustic reflectance with respect to frequency. In particular, the measured acoustic reflectance has a null indicative of resonance of the tympanic membrane at a given frequency and amplitude. The measure of the rate of change around the null is a particularly useful indicator.

In another embodiment of the invention, acoustic reflectance is measured by generating a plurality of incident sound waves, wherein each incident sound wave has a different fundamental frequency. Sound waves from the sound source and sound waves reflected by the ear are received and combined to provide an electrical signal indicative of a sum of the received sound waves. An envelope of the electrical signal provides the measured acoustic reflectance. The envelope may be detected by determining frequency domain components of the electrical signal from the transducer corresponding to the frequency of the incident sound waves. In particular, such frequency domain components may be determined by computing the energy of the electrical signal corresponding to the first coefficient of a Fourier series representing the electrical signal.

Measuring the shape of a region of the measured acoustic reflectance may also be done by measuring a rate of change of a frequency domain component of the acoustic reflectance. This frequency domain component may be the first coefficient of a Fourier series representing the acoustic reflectance. Where the measured acoustic reflectance is determined by measuring energy in an electrical signal corresponding to the fundamental frequency of the incident waves, this measured acoustic reflectance may be differentiated to obtain a measure of shape. In one embodiment, the steepest slopes around the null define an angle which provides the desired measure of shape.

The measure of shape may be used alone as the basis for diagnosis. This measure may be simply displayed to a user or compared to one or more thresholds defining ranges in which a particular diagnosis is probable, such as otitis media, middle ear effusion, abnormal pressure in the middle ear or conductive hearing loss.

BRIEF DESCRIPTION OF THE DRAWING

In the drawing,

FIG. 17 is a scattergram plotting an angle measured about the null with respect to threshold voice audiometry values in decibels for a number of patients;

FIG. 19 is a table comparing spectral gradient vs. reflectivity from acoustic reflectance curves obtained for a number of ears;

DETAILED DESCRIPTION

The present invention will be more completely understood through the following detailed description which should be read in conjunction with the attached drawing in which similar reference numbers indicate similar structures.

Figure 1:
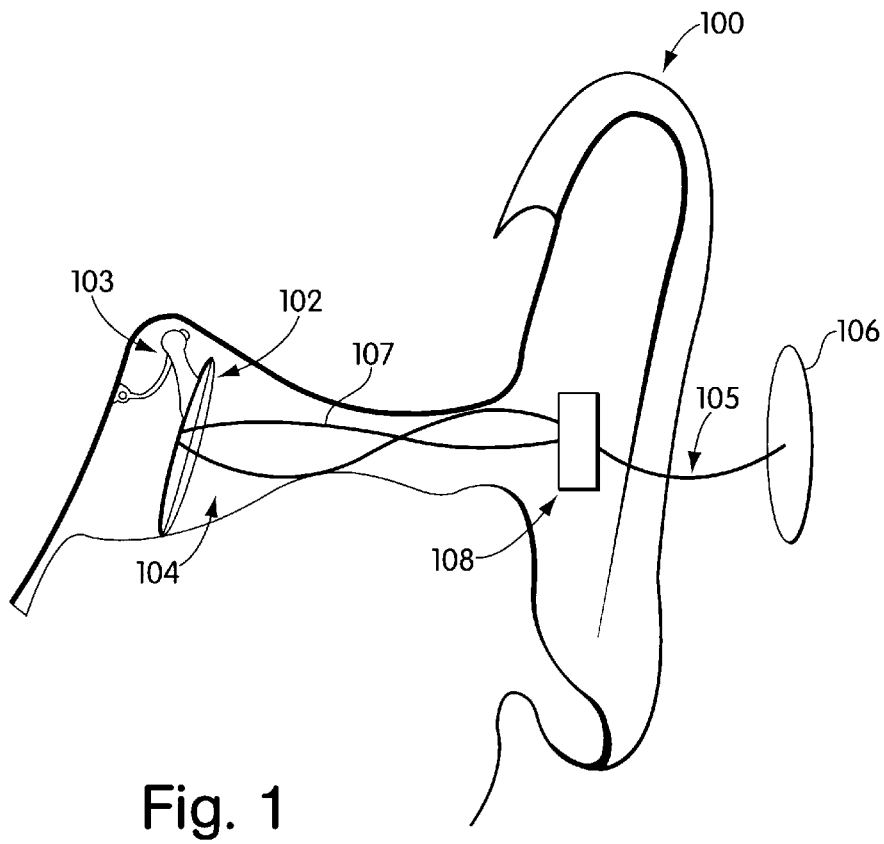
FIG. 1 is a cross sectional diagram of an ear illustrating the principle of acoustic reflectance applied to a normal ear.

The process of measuring acoustic reflectance of an ear will first be described in connection with FIGS. 1–5D. FIG. 1 shows a typical ear 100 having a tympanic membrane (an ear drum) 102, an ear canal 104, and middle ear 103. To measure acoustic reflectance, a low amplitude tone at a given frequency, indicated by line 105, is generated by an acoustic transducer, shown schematically at 106. The acoustic transducer generates sound waves for several frequencies, typically in the range of 500 hertz to 20 kilohertz. The low amplitude sound wave enters the ear canal and is incident on the ear drum 102. This sound wave is absorbed in part and reflected in part by the ear structures, including the tympanic membrane, oscicles, middle ear cleft and other components of the middle ear. The amplitude and phase of the reflected sound waves from these components are a function of the test frequency used and the complex acoustic impedance of the ear structures. In a healthy ear, some minimal reflection from the tympanic membrane and middle ear is expected. The complex acoustic impedance of the middle ear, in turn, depends very strongly on the conditions within the middle ear, and in particular on whether there is effusion, such as fluid, or abnormal pressure present within the middle ear. The vibration of a normal ear drum absorbs approximately half of the incident waves, resulting in weak reflected waves indicated by a line 107. A microphone 108 receives both the incident wave 105, the reflected wave 107 and reflected waves from ear components and as a result obtains a vector sum of the values.

Figure 2:
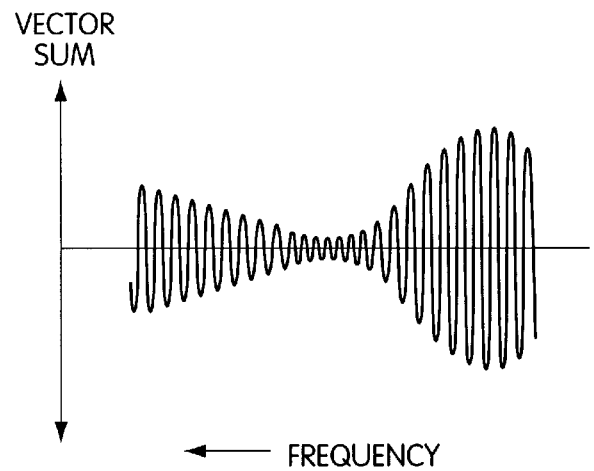
FIG. 2 is a schematic diagram illustrating a typical vector sum of the incident and reflected waves over a plurality of frequencies.
Figure 3:
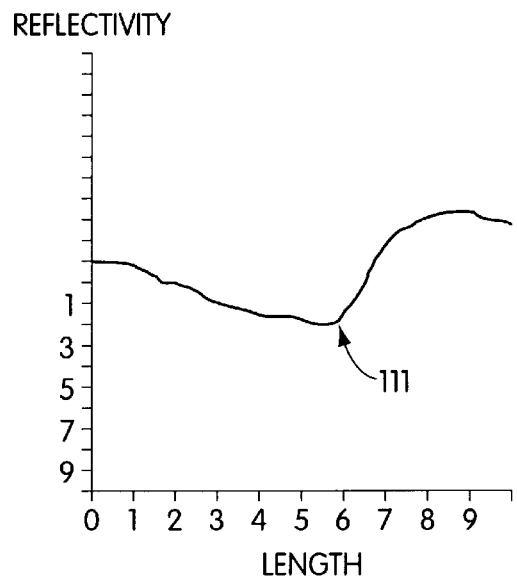
FIG. 3 is a graph illustrating an envelope of the vector sum shown in FIG. 2.

FIG. 2 represents the vector sum over a sweep of several frequencies, shown with decreasing frequency. This graph schematically shows a time domain raw data of the vector sum obtained from measuring an ear phantom. A rise, sharp fall to a null and then rise again is the characteristic resonance response of the tympanic membrane of an ear or, in this case, the ear phantom. The envelope of this curve is then determined to provide a measurement of the acoustic reflectance. This envelope can be determined in a number of ways. An envelope corresponding to the graph of FIG. 2 is shown in FIG. 3. In the graph of FIG. 3 reflectivity is shown on the ordinate and the wavelength of the incident wave is on the abscissa. The graph is similar to a printout from the Model 501 Acoustic Otoscope with a recorder. A null point 111 is found in this envelope. On the scale shown, the level of this null is at about 2.0 units.

Figure 4:
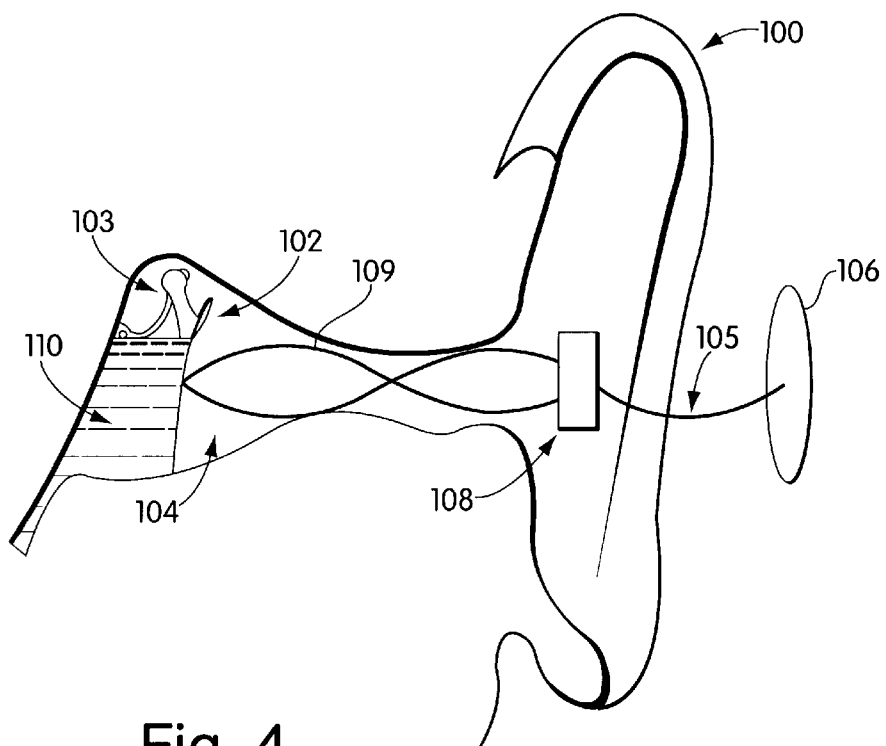
FIG. 4 is a cross sectional diagram of an ear illustrating the principle of acoustic reflectance as applied to an ear with an effusion.
Figure 5A:
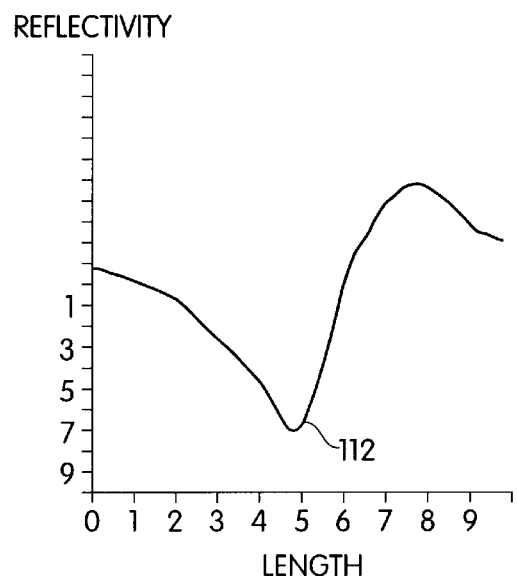
FIGS. 5A–5D are graphs illustrating typical envelopes of vector sums obtained for an effused ear.

Referring now to FIG. 4, an ear 100 is shown to have effusion 110. The middle ear effusion limits ear drum vibration which causes large reflective waves as indicated at 109. The envelope of a vector sum of incident waves 105 and reflective waves 109 has a null at the quarter wave length points, as shown in FIG. 5A. In FIG. 5A, the maximum reflectivity, i.e., the minimum of the envelope of the vector sum, are about 7.2 units using the reference system of the commercially available Model 501 Acoustic Otoscope, as indicated at 112. In this example, the point with the lowest value, or highest reflectivity, is the minimum value over all frequencies of the envelope of the vector summation signal from the microphone. The reflectivity at the null point generally indicates middle ear problems when it is greater than 5.0 units on the scale of the Model 501 Acoustic Otoscope.

In this invention, the shape of a region of the acoustic reflectance curve, defined by at least two points on the curve, is measured electronically to obtain an indicator of ear condition which is substantially independent of the line of sight between the sound source and the tympanic membrane. The indicator may be a measure of the rate of change of the acoustic reflectance with respect to a change in frequency on either or both sides of the null, around the null, of other regions of the curve or of the entire curve. The area around the null is where the curve has a significant negative slope, defining entry into the null, to a point just before the null, and after the null, where the curve has a significant positive slope, defining the exit of the null. The null typically occurs near the resonance frequency of the ear. The significance of this measurement will now be described.

As the sound wave incident to the tympanic membrane approaches a frequency where its quarter waves are coincident, the amplitude of the reflected sound waves summed with the incident sound wave approaches an amplitude null. Generally speaking, normally conducting ear drums without fluid or abnormal pressure in the middle ear demonstrate a relatively shallow acoustic null. Conversely, fluid or abnormal pressure in ears causes a stronger reflection and therefore a deeper acoustic null. The depth of this null is dependent, however, on the line of sight to the eardrum. It has been discovered, however, that the rate of change of the acoustic reflectance between the entry into the null and the exit from the null is steeper for ears having middle ear fluid or pressure than for healthy ears. It was further discovered that differences in this rate of change due to changes in line of sight have less of an impact on the indication of the presence of an effusion or abnormal pressure.

Figure 5B:
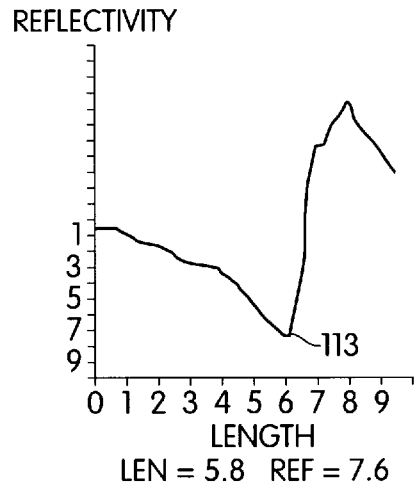
Figure 5C:
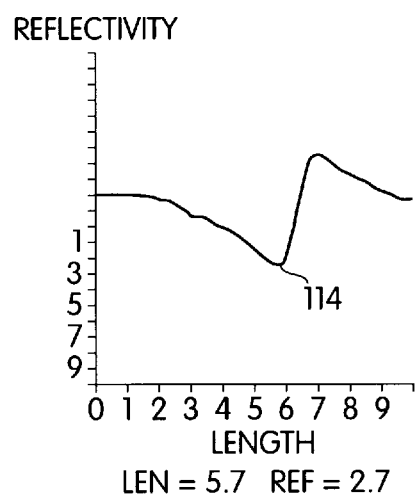
Figure 5D:
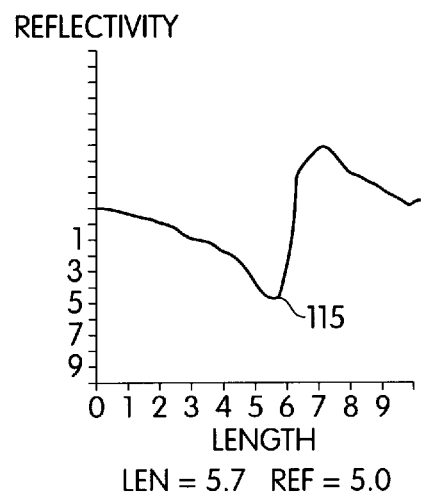

Referring to FIG. 5B, this graph shows a typical output of a Model 501 Acoustic Otoscope with a recorder for an effused ear. This measurement was made by an experienced user who had a direct line of sight to the tympanic membrane. FIG. 5C however shows the output for the same ear with a deliberately poor line of sight. Finally, FIG. 5D shows the output for the same ear that is similar to that obtained by a typical inexperienced user. The amplitudes of the outputs for the same ear from FIGS. 5B through 5D vary from 2.7 indicated at 114 according to the Model 501 scale in FIG. 5C (typically considered normal), through 5.0 at 115 in FIG. 5D to 7.6 at 113 in FIG. 5B (typically considered as indicating severe middle ear effusion), whereas the rates of change, i.e., slopes, before and after the null remain relatively unchanged.

Ear drums that are free to vibrate with the incident sound wave (i.e., healthy) produce not only a lower level reflection amplitude but also a less steep slope at frequencies around the acoustic null and thus a smaller spectral gradient. The unrestrained motion produces lower reflectance values relative to the peak null at nearby frequencies and therefore an apparent lower slope.

When the ear drum motion is restrained, (i.e., the ear is not healthy) the slope around the null is steeper. Because acoustic reflectance is related to the complex acoustic impedance of the tympanic membrane, the measure of its rate of change with respect to frequency input is analogous to measuring the "Q" of an electrical circuit. Thus, restraining the ear drum results in both a higher acoustic impedance and a sharper "Q". The "Q" is relatively constant for a given impedance regardless of the amount of energy incident due to line of sight limitations.

Figure 6:
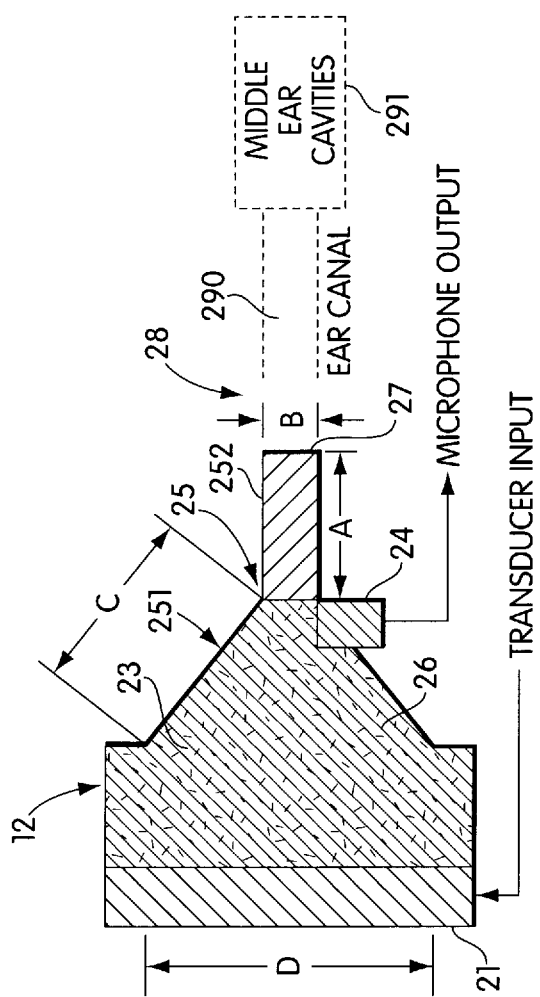
FIG. 6 is a cross sectional diagram of a suitable test head for use with the present invention.

A device in accordance with the invention will now be described. FIG. 6 is a cross sectional diagram of a test head for an instrument in accordance with the invention. The test head 12 includes a transducer 21 that creates a sound field in sound cavity 23. Sound in the cavity 23 is channeled through probe 25 to the vicinity of the ear canal 290. The probe has a funnel-shaped section 251 and an optional linear section 252. Section 252 may be chosen to match the dimensions of the typical healthy ear canal under test. This thereby matches the impedance of the probe tip and the typical ear canal. For children's ears, length A of the linear portion 252 of the probe preferably is equal to approximately 1 cm and inner diameter B of the same section should be in the range of approximately, 0.25 to 0.75 cm. Similarly, good results are obtained when length C along the side of portion 251 of the probe is about 5 cm and the approximate outer diameter D of the large end of the probe which is in contact with the sound cavity wall, is approximately 7 cm. With appropriate compensation, tips with other exit diameters may be used. The probe extension does not need to be inserted into the ear canal. In practice there may be a narrow gap 28 between the test head probe tip 27 and the entrance to the ear canal 290. Control of this gap may be facilitated by a sponge rubber spacer (not shown) attached at the end of probe tip 27.

The incident sound wave created by transducer 21 in the test head emanates from the test head at the tip 27 of the probe 25 and enters the ear canal 290. Thereafter, a portion of the incident wave is reflected by structures of the ear. Minimal reflection from a healthy ear can be suppressed by suitable selection of the inner probe tip diameter, e.g. by enlarging it to 1.0 cm for children.

Portions of the reflected waves enter at tip 27 into the hollow probe 252 of the test head. The microphone 24 is located within the test probe 25 at the junction of the straight section 252 and the conical section 251. As a result, the microphone 24, in effect, measures the net sound pressure at this point; this net sound pressure is the vector sum of the incident and reflected signals. In order to reduce internal sound reflection and resonances within the test head, the sound cavity 23 may be filled with acoustic absorbing materials.

Figure 7:
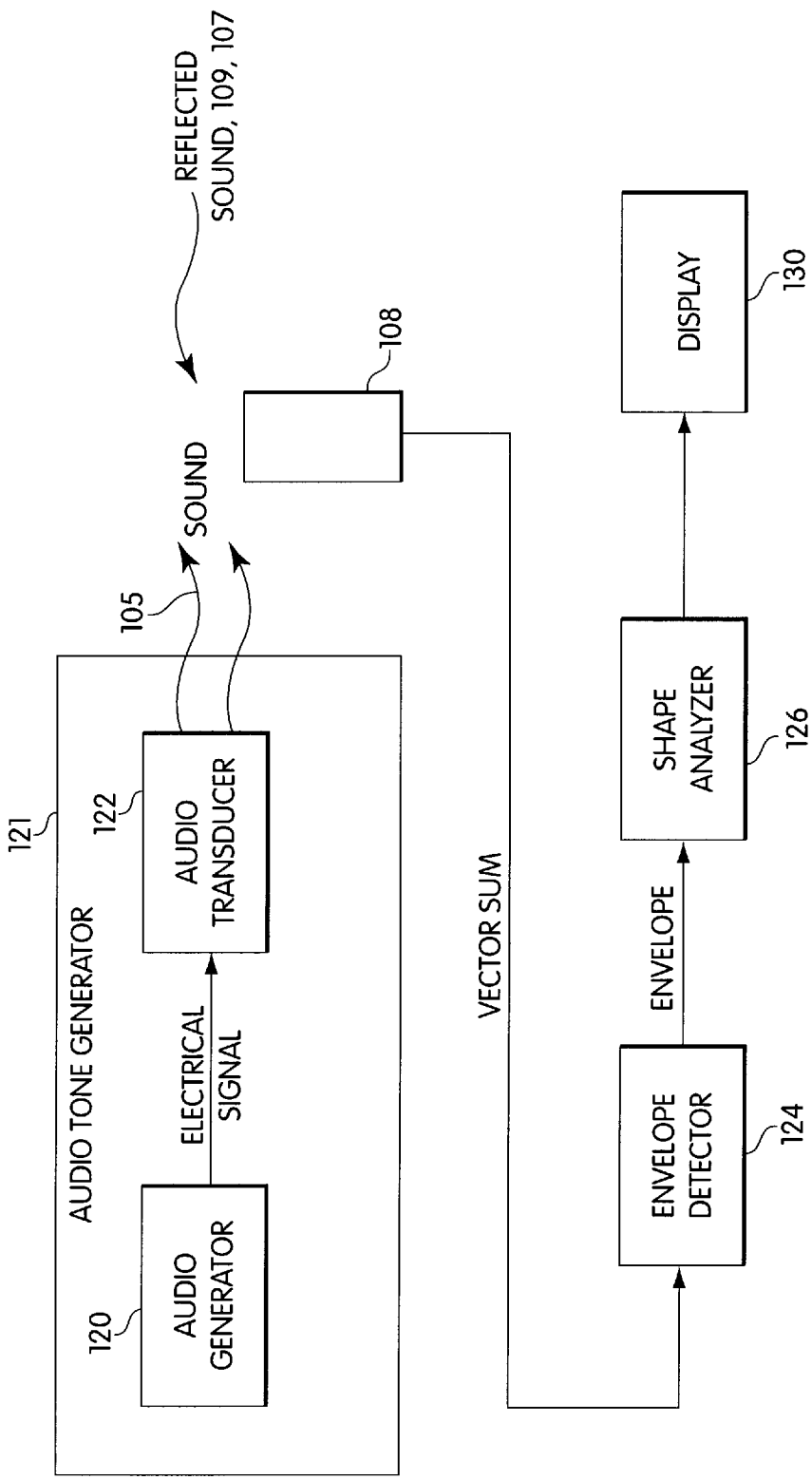
FIG. 7 is a block diagram describing a system in accordance with the present invention.

Having now described the general principles of acoustic reflectometry, and a suitable test head for use in an acoustic reflectometer, electronic circuitry suitable for practicing the present invention will now be described in connection with FIGS. 7–12. A general block diagram of a device in accordance with the invention, including its electrical and mechanical components, will now be explained in connection with FIG. 7. The components of this circuit may be implemented using a microprocessor, except for the display, acoustic transducer and microphone. An analog implementation may also be made. In FIG. 7 an audio tone generator 121 includes an audio generator 120, which produces an electrical signal which is applied to an audio transducer 122 (such as transducer 21 in the test head of FIG. 6). The audio transducer, in response to the electrical signal, generates a low level acoustic sound wave (105 in FIGS. 1 and 4) which is applied to the outer ear canal. The audio transducer 122 may be an electronic earphone, electromagnetic earphone, or other type of transducer. The transducer may be a small loudspeaker such as used in high fidelity sound headsets.

A portion of the incident sound wave is reflected by ear structures as described above. These reflected waves are summed with an incident wave by microphone 108 (such as microphone 24 of the test head of FIG. 6). The microphone may be a condenser microphone, an electrostatic microphone or other kind of microphone. The signal output by the microphone represents the vector sum of the incident wave and the reflected sound waves, having a voltage which is inversely proportional to the amplitude of the reflected waves as shown schematically in FIG. 2.

An envelope detector 124 converts the vector sum represented by the signal output by the microphone to an envelope signal represented by a voltage which varies with the frequency of the incident wave. The envelope detector 124 may be implemented as a peak value envelope detector, a root-mean square (RMS) voltage detector, or analog-to-digital converter, such as may be found in part of a microprocessor. In one aspect of the invention described in more detail below, the envelope is detected using information about the frequency spectrum of the vector sum. The envelope so detected is called the acoustic reflectance curve.

A shape analyzer 126 electronically measures the shape of a region of the acoustic reflectance curve to obtain an indicator of ear condition which is substantially independent of the line of sight from a sound source to the tympanic membrane. This information may be a measure of the rate of change of acoustic reflectance with respect to a change in frequency around the null, on either side of the null or on a region of the curve or of the entire curve. This measure may be an angle, gradient, slope, width, or other measure of the shape of the acoustic reflectance curve determined in a manner to be described below. This information is then displayed in a suitable format by display section 130.

In FIG. 7, a memory (not shown) may be added to store results of processing of one acoustic reflectance curve. With such a memory, the circuit may be operated to perform automatically a number of tests sequentially on the ear. The best result for the sequence of tests may be kept and the others may be discarded. For example, the best result could be defined as the measurement of the shape of the acoustic reflectance curve having the deepest null value. In this manner, a user of the device may attempt to get the best result with little effort.

The audio generator 120 will now be described in more detail in connection with FIGS. 8A–8C. The output of the audio generator 120 to be applied to the audio transducer 122 is a series of sine waves swept over a range of different frequencies. Typically, the sweep may be in a range from 500 hertz through about 20 kilohertz. Ranges of 1 kilohertz to 15 kilohertz, 1.8 kilohertz to 7 kilohertz, and 1.8 kilohertz to 4.4 kilohertz are acceptable. A typical period for a full sweep may range from 20 milliseconds to about 10 seconds. These are, however, only example figures. In general, there should be a frequency output that covers one or more of the resonant points of the ear canal "transmission line" as "terminated" by the middle ear. These points occur regularly at multiples of one quarter wavelength. The following resonant points have been found to be particularly useful for screening purposes: ¼ wave, ½ wave, ¾ wave, and one wavelength. In a normal adult ear these wavelengths correspond to frequencies of approximately 3.5, 7, 10.5, and 14 kilohertz.

Figure 8A:
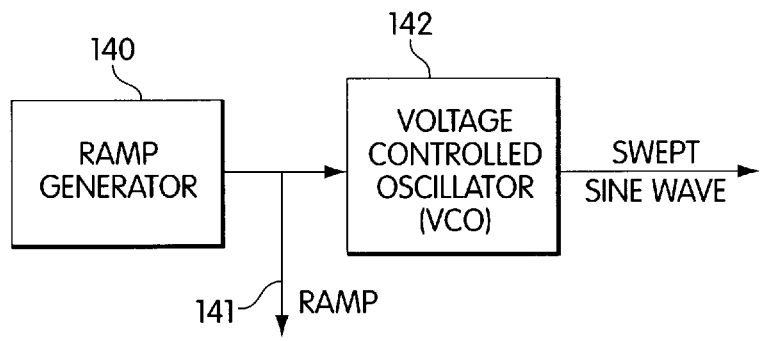
FIGS. 8A–8C are block diagrams of circuits for generating electrical signals for controlling the acoustic transducer of FIG. 7.

In FIG. 8A, the audio generator 120 (FIG. 6) is implemented using a ramp generator 140. The ramp generator 140 generates a ramp signal 141, i.e., a monotonic signal, which drives a voltage controlled oscillator (VCO) 142. The ramp signal is also used by the envelope detector 124 and the display 130 as described below. The VCO 142, in response to the ramp signal, provides a swept sine wave having a range of frequencies defined by the ramp signal. The swept sine wave is applied to the audio transducer 122.

Figure 8B:
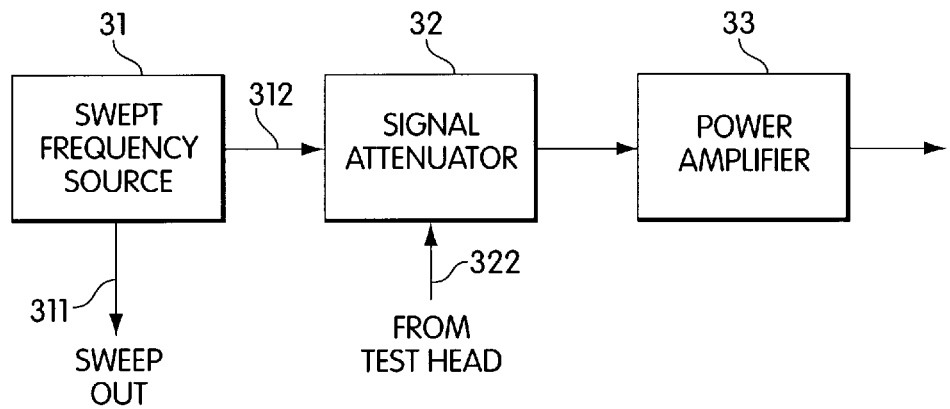

FIG. 8B is a block diagram of the audio generator 120 in an embodiment utilizing analog techniques with a continuous sweep system. A swept frequency source 31 provides a swept frequency output over line 312. The sweep signal itself appears as an output over line 311 for use in controlling the envelope detector 124 and display 130. The sound pressure from the transducer is kept at a constant level by feedback from the test head over line 322 to an attenuator 32. The voltage-controlled attenuator in this embodiment is continuously adjustable to a maximum of 20 decibels. Its output is provided to a power amplifier 33 which controls the audio transducer.

Figure 8C:
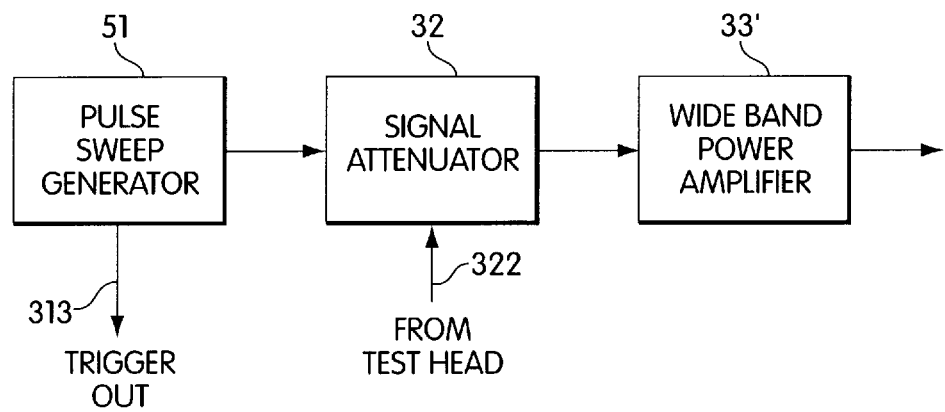

In the embodiment of FIG. 8C, a train of pulsed signals is used, each pulse at a different frequency. Components bearing numbers corresponding to those numbers discussed in connection with FIG. 8C function in a manner analogously to their correspondingly numbered components in FIG. 8B. In the embodiment shown in FIG. 8C, however, the signal to the test head originates with the pulse-sweep generator 51. This pulse-sweep generator provides a series of pulses, each of which has a width of approximately 10 milliseconds, with a pulse repetition rate of approximately 100 hertz. Each pulse has a different center frequency, the first pulse having a frequency of approximately 1.8 kilohertz. Each succeeding pulse has a center frequency proportionately higher than its predecessor pulse, until the final pulse in a given train of pulses has a frequency of approximately 4.4 kilohertz. A sequence of about 44 pulses of different frequencies is suitable. A complete screening measurement can be made with about a 0.5 second long burst of these pulses of sine waves. Preferably, a microcontroller synthesizes a burst of several cycles for each sine wave frequency at discretely timed steps. The sequence of pulses are applied to the signal attenuator of which the output is applied to a wideband power amplifier 33. The trigger out signal 313 from the pulse sweep generator is used by the display 130.

It should be understood that these embodiments of the audio generator 120 are exemplary only. Other embodiments are also possible. For example, frequency domain methods for generating an envelope, described below, do not require a sequential generation of probe frequencies with individual measurements at each discrete frequency. Broad band acoustic excitation with adequate energy distribution in the frequency range of interest also results in good frequency domain measurements using transforms to the frequency domain, such as Fourier transforms and other similar methods. White noise generation may accomplish this spectral energy distribution.

Figure 9A:
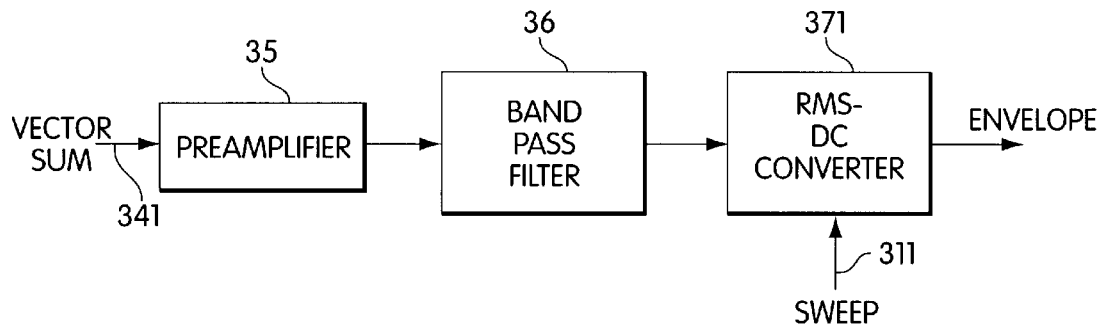
FIGS. 9A–9C are block diagrams of circuits implementing the envelope detector of FIG. 7.

The envelope detector 124 will now be described in more detail in connection with FIGS. 9A–9C. In the embodiment shown in FIG. 9A, the envelope is determined by root-mean-square to direct current (RMS-to-DC) conversion. In FIG. 9A, the output from the microphone is sent over line 341 from the test head 34 through a preamplifier 35 to a bandpass filter 36. The bandpass filter typically passes signals from approximately 500 Hz to 20 kHz. The output of the bandpass filter 36 is input to an RMS-to-DC converter 371, which outputs a measure of the total energy of the vector sum signal from the microphone for the frequency of each incident sound wave. The RMS-to-DC converter 371 is controlled, in this embodiment, by a sweep out signal 311, such as from the swept frequency source of FIG. 8B.

Figure 9B:
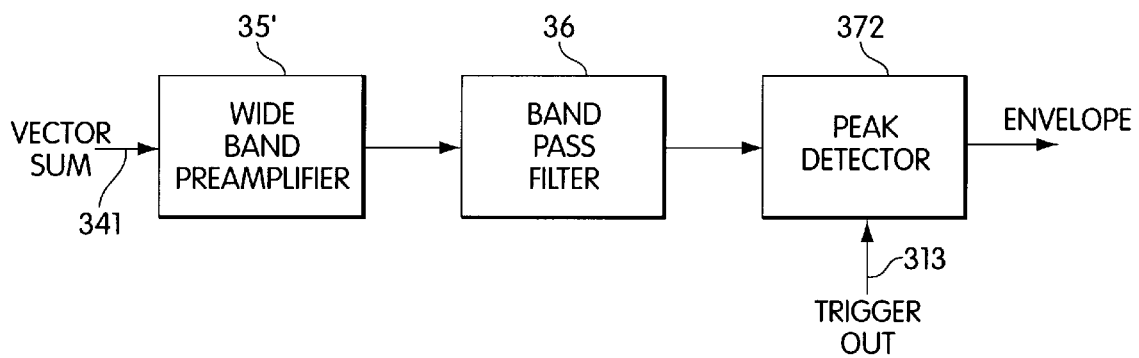

The embodiment of FIG. 9B is based on peak detection. In FIG. 9B, similar to FIG. 9A, a wide band preamplifier 35 receives the output of the microphone. The output of the preamplifier is passed through bandpass filter 36. The output of the band pass filter is input to a peak detector 372 which generates the envelope by extracting the peak value for the frequency of each incident sound wave. This peak detector may be controlled, for example, by a trigger out signal such as from a pulsed sweep generator 51 shown in FIG. 8C. One difficulty with this embodiment is that it is particularly sensitive to noise transients.

Figure 9C:
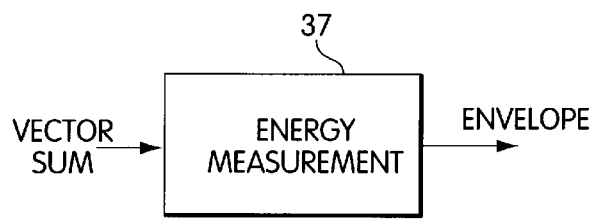

The embodiment shown in FIG. 9C uses frequency domain information of the vector sum to determine the envelope. This embodiment is based on the principle that an acoustic signal, or its electrical analog, may be represented by a series of sine waves of different frequencies (the Fourier series). Each frequency has an associated coefficient that determines its overall amplitude. Summing all the coefficients of the Fourier series reproduces the original wave shape. The first coefficients are the fundamental frequency. The higher coefficients of a pure sine wave are zero. In this embodiment, the series of sound waves generated by the acoustic reflectance instrument is a series of sine wave bursts of several cycles, with each burst at a different frequency. Knowing the fundamental frequency of each burst, the first coefficients of that signal represent only the fundamental frequency. All other frequencies can be ignored.

Ignoring all frequencies other than the fundamental frequency, the energy of the received vector sum signal may be expressed as the sum of the squares of the Fourier coefficients of the fundamental frequency. These coefficients are the products between the vector sum signal and the sines and the cosines of the fundamental frequency. The energy is thus defined by equation (1) below:

$$E_f[\Sigma V_x \times \sin.(2\pi f)]^2 + [\Sigma V_x \times \cos.(2\pi f)]^2 \qquad (1)$$

where $E_f$ is the energy at the incident frequency f, and $V_x$ is the vector sum voltage. The summation symbol indicates that this product is calculated for each sample of the vector sum voltage over an integer number of cycles of the vector sum signal. This energy of the fundamental frequency of the acoustic wave is measured by energy measurement section 37 in FIG. 9C. The square root of the energy value $E_f$ yields the RMS value of the component of the signal that contains only the fundamental frequency. The envelope is defined by the RMS value for each incident frequency.

One benefit of this embodiment is that measuring the energy of the vector summed signal for the fundamental frequency over several cycles should substantially reduce effects of external noise and provides a meaningful quantitative value associated with that frequency. Thus, the measured energy at each of the incident frequencies provides a relatively noise-free envelope of the tympanic membrane's resonance characteristic in response to the series of incident sound waves. Thus, sounds from a crying child and ambient room noise are eliminated if their frequency content is not at the fundamental frequency being measured.

It is also useful in this invention to normalize the envelope detected by envelope detector 124 to account for nonlinearities of the acoustic system, including the microphone, transducer, acoustic chamber and tip, from which the vector sum is obtained. This normalization is based on an assumption that if the incident waves were applied to open air, there should be no measured reflection. Thus, the resulting curve of the vector sum and its envelope should be flat. However, due to nonlinearities in the acoustic system, the resulting curve is typically not flat.

Figure 10A:
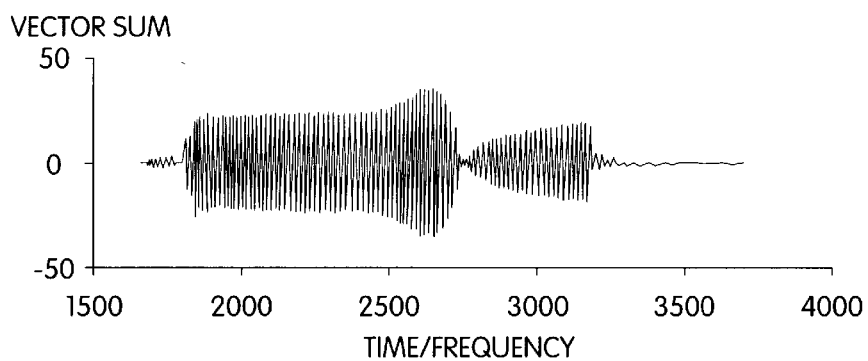
FIGS. 10A–10B represent the vector sum and corresponding envelope of the reflectance from an effused ear using a device in accordance with the invention.
Figure 10B:
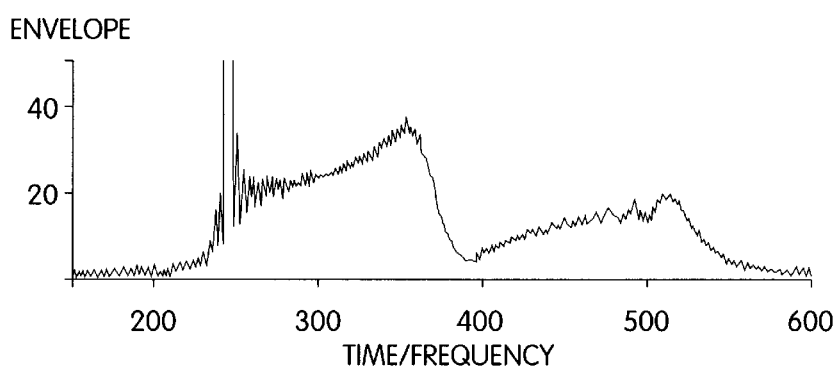
Figure 10C:
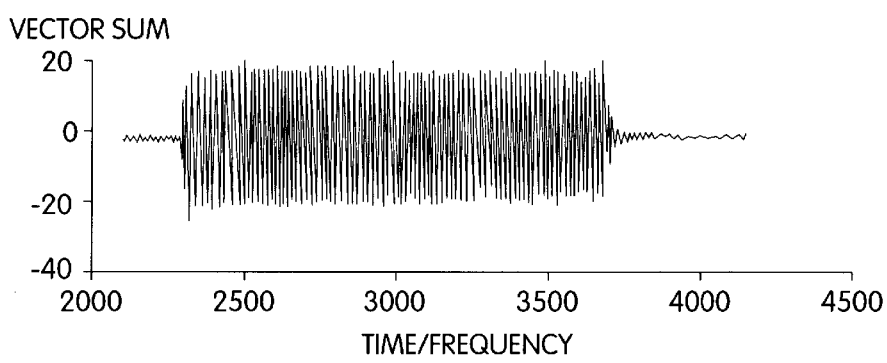
FIGS. 10C–10D represent the vector sum and corresponding envelope of the reflectance from open air using a device in accordance with the invention.
Figure 10D:
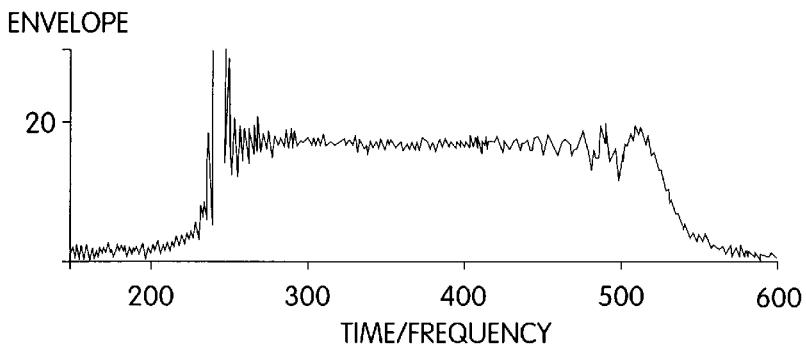

For example, an actual vector sum obtained with a device using a continuous sweep audio tone generator as applied to open air is shown in FIG. 10C. In this Figure, the abscissa represents either increasing time or the frequency of the incident wave in arbitrary units. The ordinate represents the amplitude of the vector sum output by the microphone in arbitrary units. FIG. 10D represents the envelope of this vector sum using the method described in connection with FIG. 9C. In this Figure, the abscissa represents increasing time or frequency of the incident wave in arbitrary units. The ordinate represents the magnitude of the envelope in arbitrary units. There are noticeable irregularities in the envelope shown in FIG. 10D.

FIG. 10A shows the vector sum as obtained from an ear phantom, a mechanical construction that is acoustically similar to an actual ear. In this Figure, the abscissa represents increasing time or frequency of the incident wave in arbitrary units. The ordinate represents the amplitude of the vector sum output by the microphone in arbitrary units. FIG. 10B is a graph illustrating the envelope of the vector sum shown in FIG. 10A detected using the method described in connection with FIG. 9C. In this Figure, the abscissa represents increasing time or frequency of the incident wave in arbitrary units. The ordinate represents the magnitude of the envelope in arbitrary units.

Before analyzing the shape of the curve shown in FIG. 10B, it is preferable to normalize the envelope shown therein using the knowledge of the irregularities of the acoustic system as shown by FIG. 10D. Thus, for each frequency for which data was stored for the acoustic system as applied to open air (from FIG. 10D), the reciprocal of the value of the envelope for each frequency is used to scale the value of the envelope at the corresponding frequency in the curve obtained for a given ear (e.g., in FIG. 10B).

Figure 11:
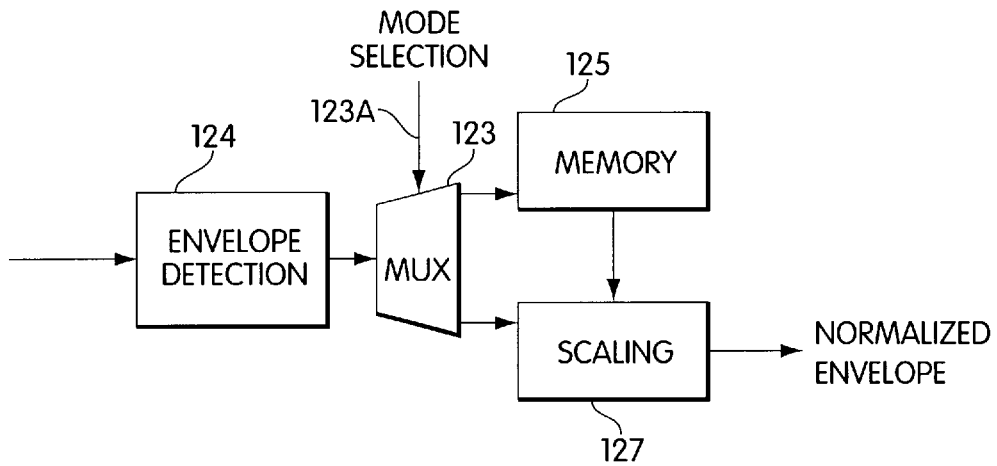
FIG. 11 is a block diagram of a circuit useful for normalizing the detected envelope for nonlinearities in the acoustic system.
Figure 12:
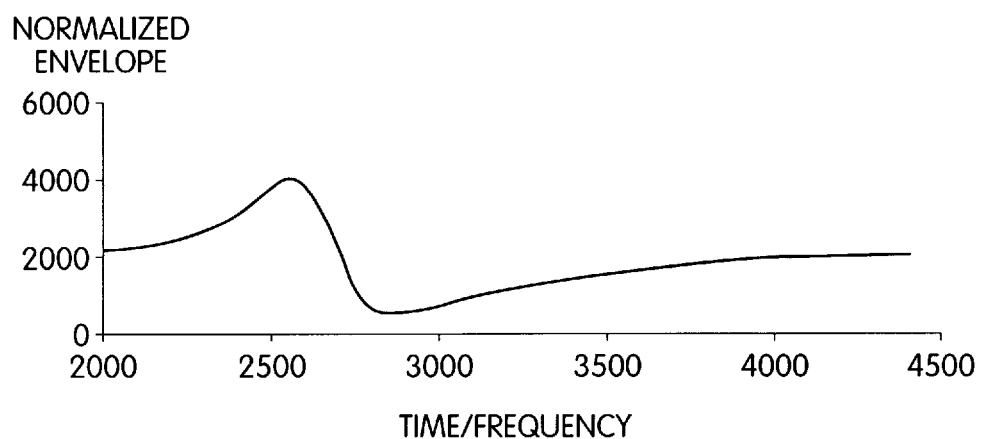
FIG. 12 is an example normalized envelope signal.

A circuit for performing this normalization is shown in FIG. 11. The envelope detector 124 has an output applied to a multiplexor or other selector which is controlled according to a mode selection signal 123A. In normalization mode, the device is directed to open air and the output of the envelope detector is stored in a memory 125. In measurement mode, when measurements on an ear are being performed, the output of the envelope detector is applied through the multiplexor 123 to a scaling section 127. For each frequency of incident waves applied to the ear, the value of the envelope at that frequency is scaled by the reciprocal of the value for the same frequency stored in memory 125 to provide a normalized envelope output. Such a normalized envelope is shown in FIG. 12. In this Figure, the abscissa represents increasing frequency in arbitrary units. The ordinate represents the magnitude of the envelope in arbitrary units. Note that the curve of FIG. 12 is substantially smoother than the envelope of FIG. 10B.

Further digital signal processing may be performed on the normalized envelope to reduce noise in the curve, or in regions of interest in the curve. For example, low pass filtering can be performed on the region having a negative slope prior to the null value, e.g. using a three-tap filter. The region having a positive slope after the null value may also be filtered, e.g., using a five-tap low pass filter. The information for an entire curve could also be discarded if insufficient amplitude is obtained for the null value. These and other kinds of digital filtering may be performed. For example, the acoustic reflectance envelope may also be scaled for use in angle measurement and waveform plotting.

The shape analyzer 126 will now be described in more detail. The shape analyzer 126 electronically measures the shape of a region of the acoustic reflectance signal. A number of regions may be of interest. The region of primary interest in the region around the null. Additionally, the portion of the negative slope at the entry of the null may also be significant and contain diagnostically useful information. The positive slope following the null and the peak-to-peak amplitude of the resonance waveform may also be useful. The shape analyzer 126 may, in addition, electronically determine the location and amplitude of the null of the detected waveform using a form of null detector which detects minimum voltage values.

There are several ways to measure the shape of a region of the acoustic reflectance curve, including measuring the gradient or slope. The shape of a region defining a dip may be measured by examining gradient or slope of the sides of the dip, or by measuring an angle defined by the dip or by measuring the width of the dip.

Methods for measuring the shape of the region of the acoustic reflectance curve around the null will first be discussed. These methods are related to measuring the slope of the line on either side of the null in terms of frequency per volts, where volts is the measure of the output from the vector sum of the microphone.

In one embodiment of the invention, the measurement of the shape of the null is presented as a measurement of an angle formed by the null in the acoustic reflectance curve as if the curve were printed by the recorder of the Model 501 Acoustic Otoscope. In order to achieve this, the acoustic reflectance curve is scaled to match the scale of the Model 501 Acoustic Otoscope. To perform such scaling, for each frequency f to be represented on the abscissa, its actual position L on the abscissa is determined by the product of its offset from the first frequency $f_o$ in the range to be displayed and the width W of the plot, e.g., 84 mm, divided by the frequency range $f_r$ as follows:

$$L=(f-f_o)*W/f_r$$

Each of the corresponding reflectivity values R is computed according to the following equation:

$$R=A*H/A1800,$$

where A is the amplitude, H is the plot height, e.g., 40 mm. These scaling formulas are merely illustrative for the Model 501 Acoustic Otoscope. Other scaling formulas could also be used.

Given the values as scaled to an appropriate reference frame, such as the display of the Model 501 Acoustic Otoscope, angles or other measurements of the shape of the null and other regions of the acoustic reflectance curve can be computed.

A first method involves a frequency gradient/amplitude reference. First, an amplitude value is established for the null apex. Second, the frequency is measured for each side at a known incremental voltage value above the null value. This incremental voltage is typically about 20% of the possible voltage output range of the envelope detector 124 (FIG. 7). Generally speaking, this incremental voltage should provide a point on the curve after entry to the null but before leveling off in the curve very close to the null point, for a typical unhealthy ear. For example, the incremental voltage may correspond to two reflectivity values on the Model 501 Acoustic Otoscope. The incremental voltage may also be made proportional to the voltage at the null value to provide for a normalization effect. The frequency at this voltage may be determined by sampling the output of the audio generator 120 (FIG. 7) or ramp generator 140 (FIG. 8A). The difference in the two frequencies is the desired result.

A second method involves a frequency increment measurement. More particularly, the frequency of the null apex is established. Then, the relative amplitude is measured at a known incremental frequency above the apex frequency. The corresponding relative amplitude is found for an incremental frequency below the apex frequency. Generally speaking the incremental frequency should provide a point on the curve after entry to the null but before leveling off in the curve very close to the null point for a typical unhealthy ear. The incremental frequency may generally be within 10 and 1000 Hz. The vector sum of the relative amplitudes and corresponding frequencies is the desired result.

Figure 13:
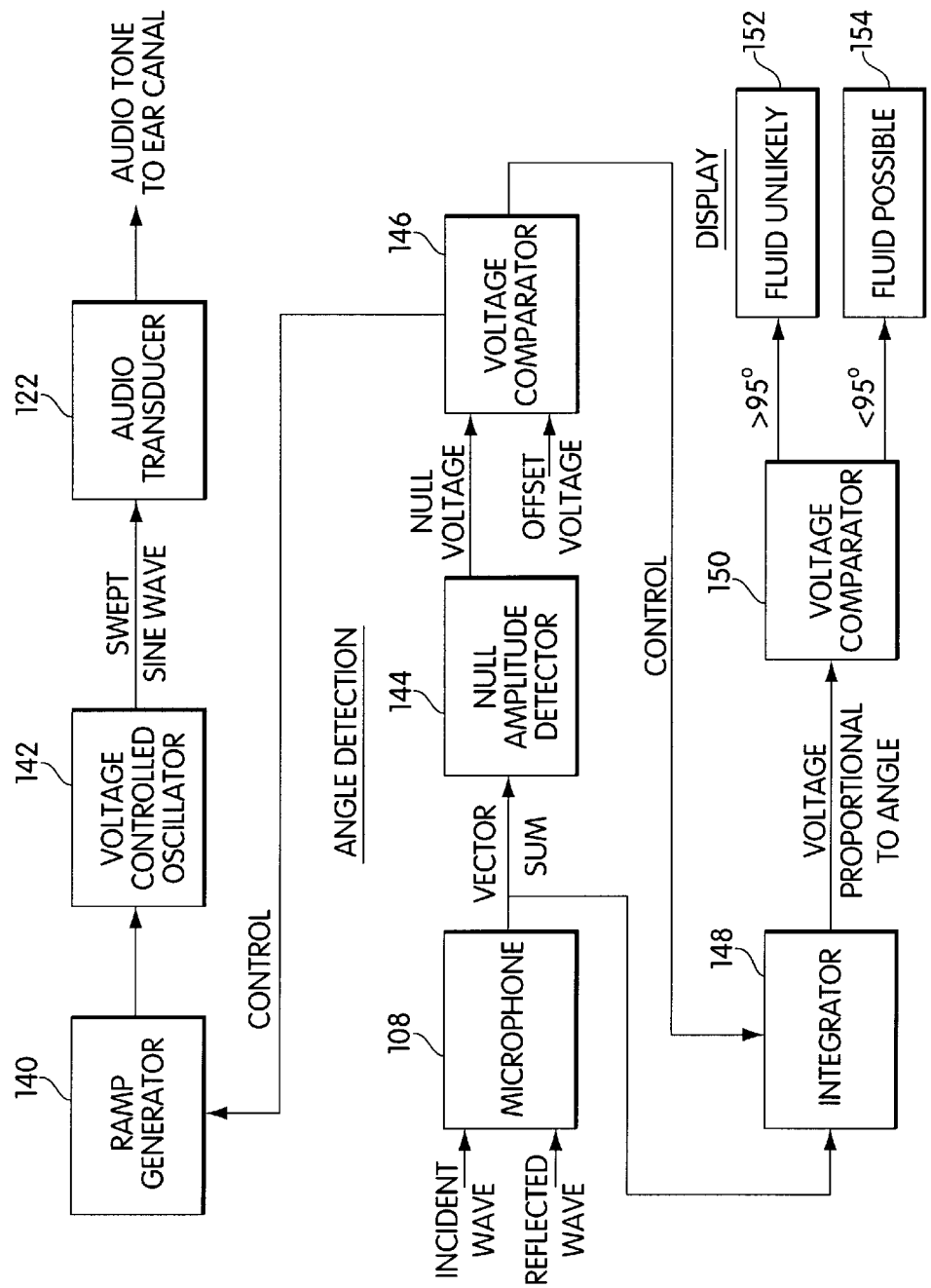
FIG. 13 is a block diagram of a circuit for implementing one embodiment for measuring the shape of a null in an acoustic reflectance curve.

A third method is called an integration measurement. With this method, after the amplitude of the null apex is established, the frequency is then scanned from an incremental voltage threshold on one side of the null to the same or similar value on the opposite side of the null. The incremental voltage may be the same as used in the first method. A current integrator is activated between the two thresholds. The resulting integrated voltage is used as a relative number. Alternatively, the output of the audio generator 120 (FIG. 7) or the output of the ramp generator 140 (FIG. 8A) may be sampled on the opposite sides of the null and the difference may also be used as the desired result. In FIG. 13, the shape analyzer detector 126 is implemented using a null amplitude detector 144 which determines a null voltage. The null voltage is applied to a voltage comparator 146 which also receives an offset voltage. The combination of the null voltage and an offset voltage act to provide a control signal back to the ramp generator 140 for uses as will be described below. Similarly, the control signal is applied to an integrator 148 for reasons to be described below. The vector sum may also be applied from microphone 108 to the integrator 148.

The operation and cooperation of the ramp generator 140, voltage comparator 146 and integrator 148 will now be described. Their co-action implements the integration method described above. After detection of a null voltage, an offset voltage above the null voltage is determined. The ramp generator is allowed to sweep through the set of frequencies one additional time. When the output voltage of the microphone meets the offset voltage, the integrator 148 is turned on and begins to perform an integration as the voltage decreases to the null voltage and then back up to the offset voltage. The value of the integrator after the second rising offset voltage is met provides a value proportional to the angle of the null. This value is provided to a voltage comparator 150 which provides an output indicative of whether the angle is less than or greater than one or more cut point angles. These outputs are applied to a display, such as to light emitting diodes 152 and 154.

Figure 14A:
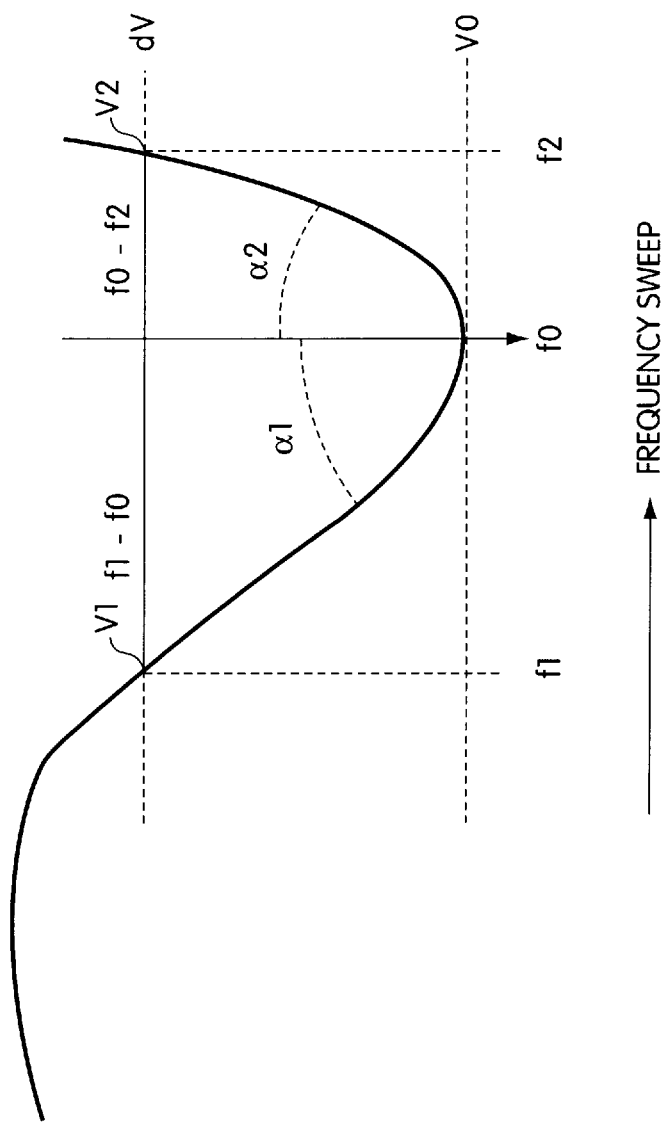
FIGS. 14A–B are graphs illustrating methods for performing an angle measurement.

Yet another method is called a slope measurement. After the frequency of the null angle apex is established, the slope of one side of the angle is measured by dividing the frequency difference by the voltage difference (or vice versa) from another point on the curve. The slope of the other side is similarly measured. The difference in slopes is used as the desired result. Transcendental functions may be used to determine the angle in degrees from this value. As an example, referring to FIG. 14, knowing both the frequency generation and null voltage calibration allows either angle, slope or gradient measurements to be made. The amplitude value (V0) and corresponding frequency (f0) at the null is stored in memory. Then the two frequencies corresponding to a given voltage offset are measured as f1 and f2. Referring to FIG. 14, the angle arctan [(f1−f0)/V0] and angle $\alpha_2$=arctan [f0−f2)/V0]. The null angle then is $_1+_2$). When the scale used to represent the acoustic reflectance curve is the same as that used for the display of the Model 501, the angle so measured corresponds to an angle as it would appear on the display of the Model 501 Acoustic Otoscope.

Figure 14B:
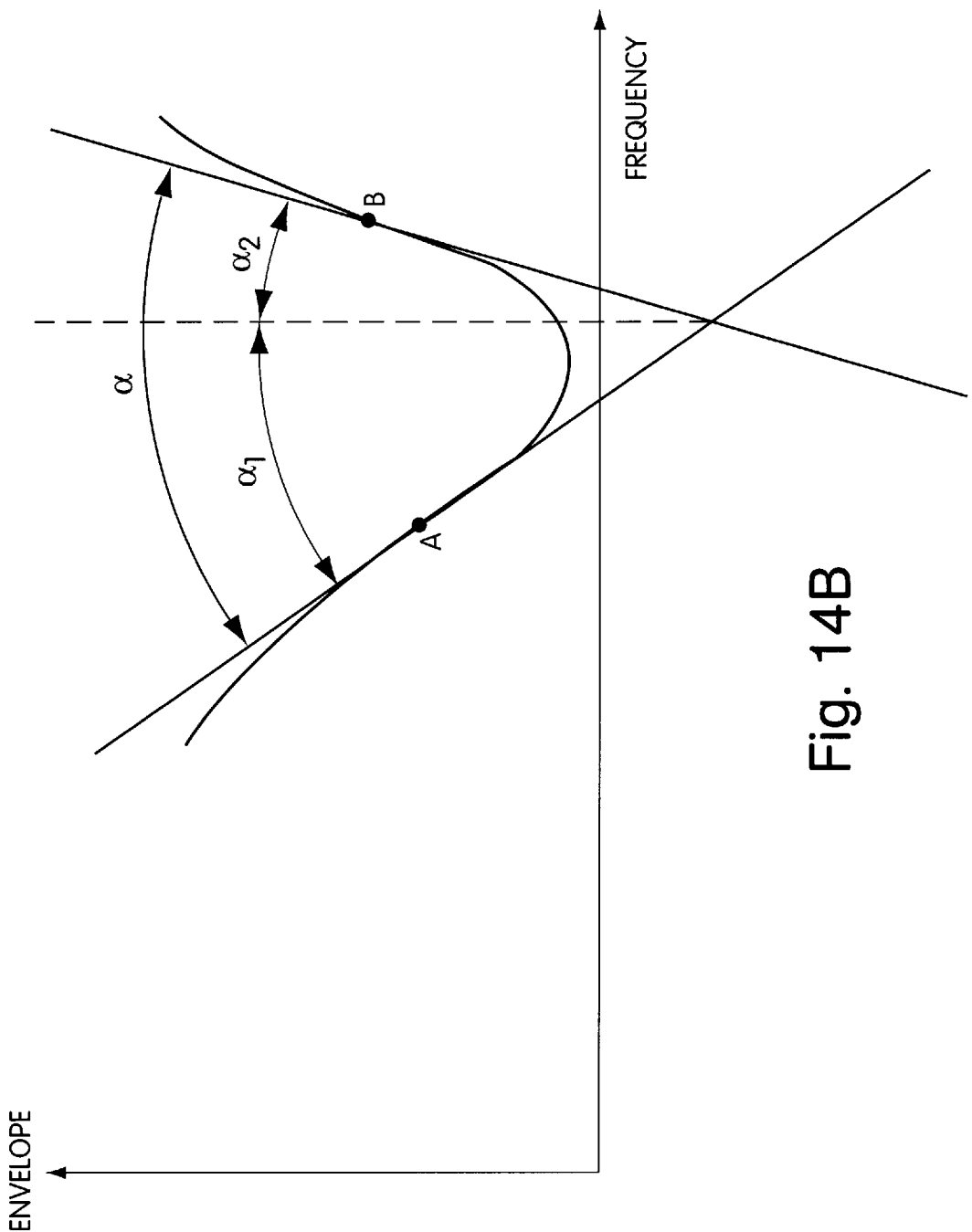

Yet another method for measuring shape of the null involves a frequency domain analysis, such as a Fourier transform analysis or similar transforms, herein called the spectral gradient measurement. The Fourier transform is a mathematical method of analyzing an electrical signal in the frequency domain as opposed to the more conventional time domain. When the envelope of the vector sum is generated using a Fourier series as described above in connection with FIG. 9C, differentiating the transformed signal results in a direct measure of the frequency gradients within the signal. Summing the angles corresponding to the steepest negative and positive gradients on either side of the null provides a direct measure of an angle around the null. In particular, as shown in FIG. 14B, for the sake of illustration, point A and point B are assumed to be the points with the steepest gradients, called "a" and "b". The angle α defining the shape of the null is the sum of angles $\alpha_1$ and $\alpha_2$. In this embodiment, in contrast to FIG. 14A, $\alpha 1 = \pi/2 - \arctan(a)$ and $\alpha 2 = \pi/2 - \arctan(b)$.

Another method for measuring shape is a wavelet analysis of the detected envelope. Wavelet analysis can be used to extract multiple features from the envelope. The features thus obtained are distinctive features of the envelope since they can be used to define the envelope. These features could then be used as the basis for diagnosis. Such features also allow classification of various envelopes using neural network and/or other pattern recognition methods. Pattern recognition methods may also be used to extract features from the envelope.

Figure 18A:
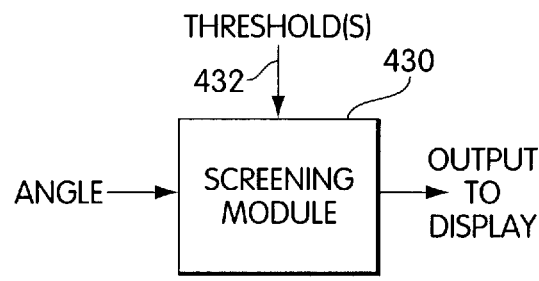
FIGS. 18A–18C are block diagrams of circuit elements for providing output to a display based on measurements of the acoustic reflectance curve.
Figure 18B:
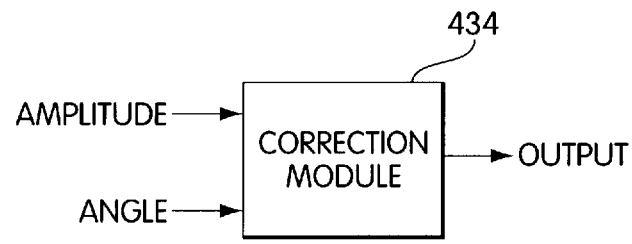
Figure 18C:
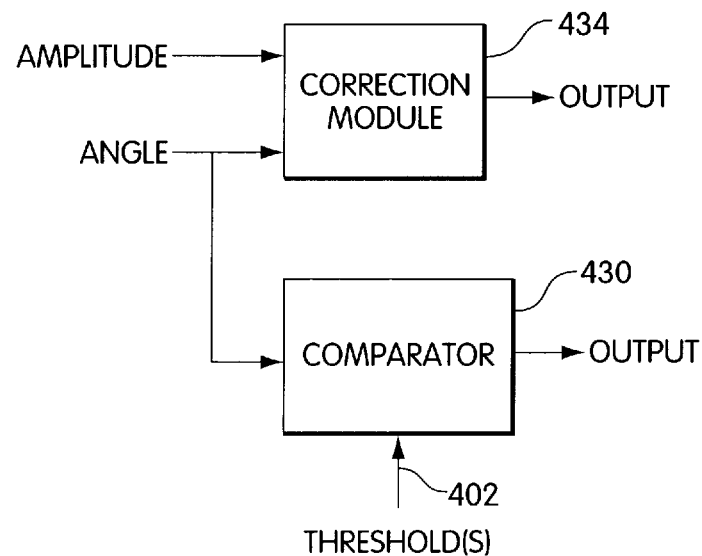

Given the information obtained by measuring the shape of the acoustic reflectance curve, an instrument having an output presenting this information in the form of a likely diagnosis is possible. For example, as shown in FIG. 18A, a screening module 430 can be used to compare an input shape measurement to a threshold 432. The result of this comparison can be presented to a user as "healthy" or "unhealthy". Another possible implementation, shown in FIG. 18B, is to use the shape information, such as an angle to weight, to correct the reflectivity or null value obtained. This correction accounts for errors due to line of sight differences. A correction module 434 receives the null value and shape information, such as an angle, and computes the corrected value to be output. FIG. 18C combines both the screening module 430 and the correction module 434.

The correction module 434 will now be described in more detail. This module can be implemented in many different ways and can perform the correction in many different ways. A typical form of a suitable function for correction of the measure of acoustic reflectance by the measured angle is:

$$ACR = \frac{AR * N}{(M + \text{Angle})}$$

where
AR=the acoustic reflectance at the acoustic null;
N=a selected constant multiplier;
M=a selected constant; and
Angle=the measured null angle.

This formula creates a suitable cut point at the midpoint reflectance value of 5.0 at an angle of 82°, with N set at 200 and M set at 118, respectively, as will be described in more detail below. The selection of the parameters of this function may be done empirically so as to maximize the sensitivity and the specificity of a given cut point.

To implement the weighting function, a microprocessor may be used to calculate a corrected value when the angle and reflectance values are input using the formula as described above. However, to accomplish both corrections described above plus make end point corrections would result in unnecessary complexity. The complexity of the microprocessor needed to perform such calculations in real time might substantially increase the cost of an instrument and the power required by the circuitry. An cost-effective alternative would be to utilize a read-only memory look up table whose input address is the two variable values: gradient and reflectance, with the corrected value stored at the location in the read-only memory corresponding to the input address. Given any input address, the corresponding weighted value is provided at the output to be displayed and printed.

Figure 15:
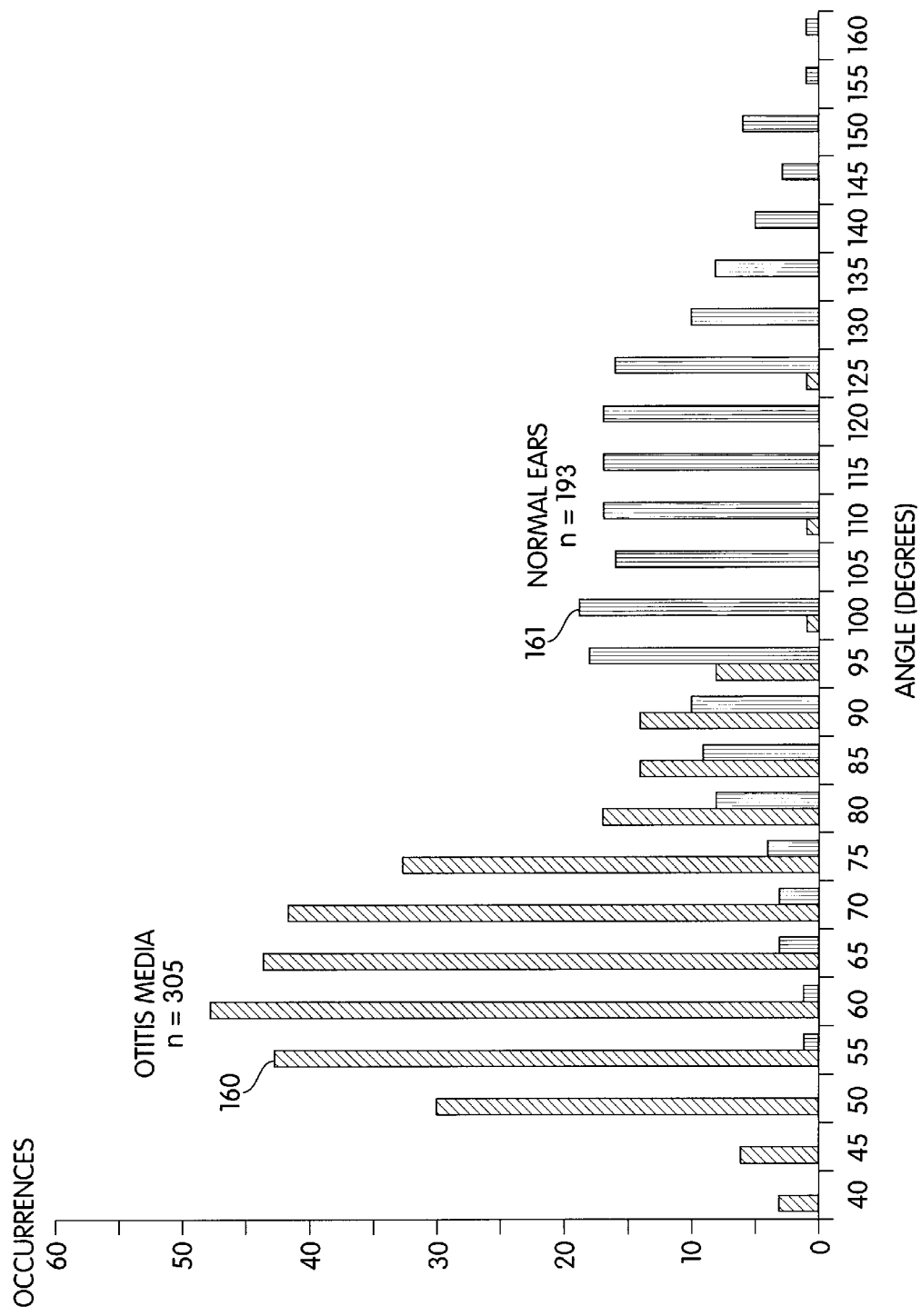
FIG. 15 is a histogram showing a number of ears based on a measured angle about the null of the acoustic reflectance curve and an ultimate diagnosis.

This invention is well-suited for a screening instrument for use by non-medical personnel. Such a screening instrument uses one or more cut-off values for the shape measurement to provide a simple output, such as "HEALTHY", "CONTINUE MONITORING" or "REFER" to a physician. It has been determined empirically, as shown in FIG. 15, that for an angle representation of the shape measurement, a threshold or suitable cut-off point above which an ear is healthy is about 95 degrees, where the angle is measured using the spectral gradient method described above. FIG. 15 is a histogram showing the number of patients (out of 498) having a given spectral gradient measurement, and grouped together according to diagnosis, i.e., whether the patient was ultimately diagnosed with otitis media or was otherwise healthy. Bars, such as 160, having diagonal hash marks, for each given spectral gradient indicate the number of patients having the spectral gradient measurement and which were diagnosed with otitis media. Bars, such as 161, having vertical hash marks, for each given spectral gradient indicate the number of patients having the spectral gradient measurement and which were diagnosed as having healthy ears. Cut points are establish which define thresholds for diagnosis. Suitable cut points are: 95 degrees, above which the patient is healthy with a high probability and 75 degrees, below which the patient has otitis media with a high probability (about 90%). The range between 75 and 95 degrees indicate patients whom should be monitored for possible development of otitis media. Other cut points below 75 degrees may also be used to increase the probability of the diagnosis, e.g., 65 degrees and 55 degrees. These cut points were selected empirically so as to simultaneously maximize the sensitivity and the specificity.

Figure 16:
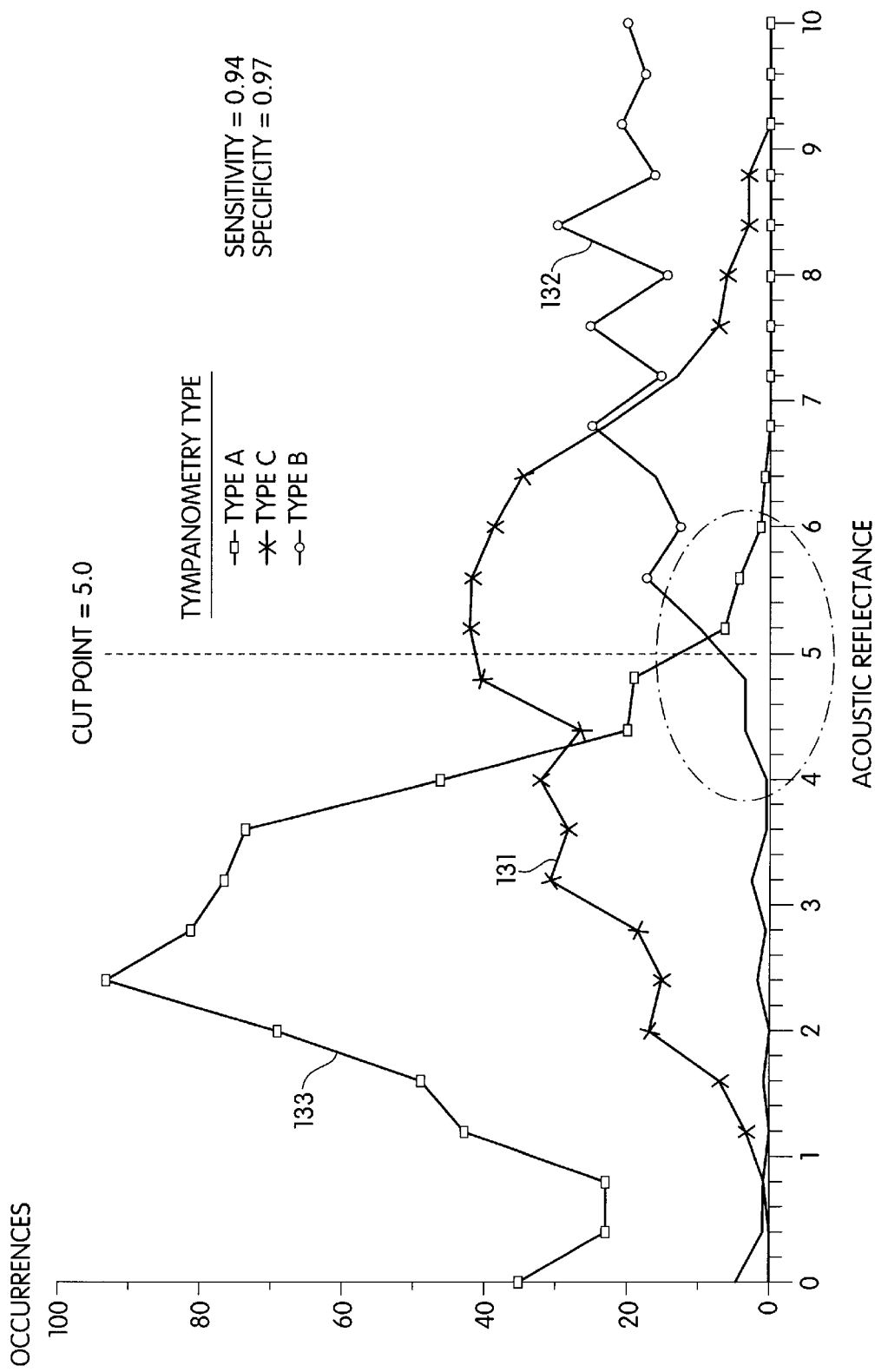
FIG. 16 is a histogram showing the probable diagnosis for ears based on a null value corrected by an angle measured about the null of an acoustic reflectance curve, as compared to tympanometry type.

FIG. 16 is a histogram based on the acoustic reflectance measurements for ears of 1393 patients, corrected by a measured spectral gradient, grouped according to tympanometry type. Correction was made using the formula described above. In this figure, curve 133 corresponds to tympanometry type A (674 patients), curve 131 corresponds to tympanometry type C (462 patients), and curve 132 corresponds to tympanometry type B (257 patients). It can be shown an acoustic reflectance value of greater than 5 can clearly distinguish between normal and unhealthy ears. For this as a cut point, a sensitivity of 0.94 and a specificity of 0.97 was obtained. It may also be advantageous to continue to use two or more cut points. An instrument for use by non-medical personnel may also be made using this information as the basis for diagnosis.

Referring now to FIG. 17, the correlation of conductive hearing loss to the angles is shown. FIG. 17 is a scattergram based on the angle of acoustic reflectance measurements and threshold voice audiometry measurements for ears of 68 patients. It is shown in this figure that all patients with an audiometry threshold of 25 dB or greater had a null angle measurement of less than 90 degrees. For this data set, a sensitivity of 1.0 was obtained. Accordingly, an instrument for use by non-medical personnel for detecting a likelihood of conductive hearing loss may also be made.

Referring now to FIG. 19, the improved independence from the line of sight for the spectral gradient measurement described above over the null value alone for diagnostic purposes will now be described. In tests from which the data of FIG. 19 was gathered, at least four measurements were taken for each ear. Average values of the null value and spectral gradient were taken, and maximum and minimum values were referenced to the average to obtain above average, below average and spread values. The spread value is the sum of the minimum and maximum differences from the average. A change in spread was determined for each ear which indicates the improvement in the spread from the null value to the spectral gradient measurement.

A significant finding is that as the spread in reflectivity values, in column 500, grew larger, the improvement of the spread in the spectral gradient measurement, in column 502, grew larger. This improvement is defined by the average ratio of reflectivity spread to the spectral gradient spread. That is, the ratio, column 502, is the percent spread of the null value divided by the percent spread of spectral gradient. For ears with a reflectivity spread of 50% or greater, the spectral gradient measurement improved the spread by an average of 45.9 percentage points; 25.4 percentage points improvement was achieved for all reflectivity spreads of 30% or greater, etc. Thus, the average improvement is nearly three to one for reflectivity spreads of 30% or greater.

Embodiments of an instrument which analyze acoustic reflectance to obtain shape measurements, including spectral gradient measurements, to provide diagnostic output to a user will now be described in connection with FIGS. 20a–20d. It should be understood that these embodiments are merely exemplary and not limiting. Other configurations are possible and will depend on the particular condition intended to be diagnosed, e.g., otitis media, effusion, hearing loss or abnormal pressure or other conditions, and the user, e.g., doctor, trained personnel or untrained personnel.

Figures 20A, 20B:
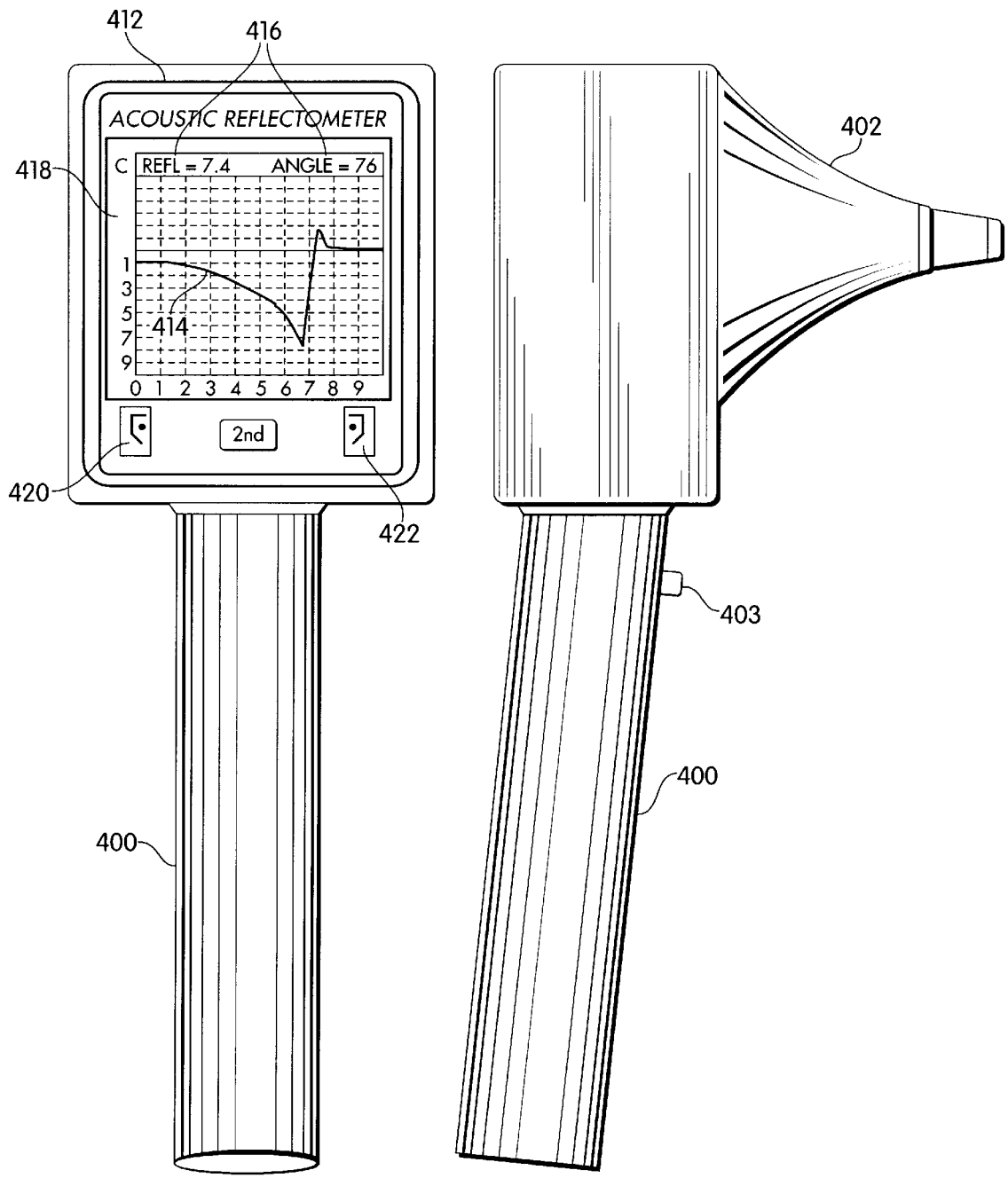
FIGS. 20A and 20B illustrate suitable packaging for a diagnostic instrument in accordance with the present invention.

FIGS. 20a–20b illustrate one embodiment of an instrument in accordance with the present invention. This embodiment is intended for use as a diagnostic product for hospital or clinical use in diagnosis of ear pathologies by trained professionals, such as doctors and other primary care providers. The device is preferably battery-operated and uses modern low-power circuitry and power conservation techniques to minimize power consumption. For example, circuits preferably are used only when required and the system automatically enters a stand-by mode when not in use.

In this embodiment, the instrument has a hand piece 400 with replaceable tips 402 that contact the patient. The shape of the hand piece is intended to more closely resemble that of the ubiquitous otoscope. A debounced measure button 403 is provided to start a sweep by the oscillator to obtain a measurement.

This output of this instrument is similar to that of the commercially available Model 501 Acoustic Otoscope, but also provides the measure of the shape of the curve. A numeric null value also may be displayed, or a corrected null value may be displayed. Therefore, the hand-held instrument displays on its output 412 both the acoustic reflectance curve at 414 and the numeric results 416 on a low power LCD graphics display 418 in relative units corresponding to the established numbers as reported in the literature. In contrast to the Model 501 output, the ear canal length number need not be shown when the entire acoustic reflectance curve is graphically displayed on the instrument.

It may also be desirable to provide an additional memory (not shown) for storing data for later retrieval. By providing sufficient memory, multiple sets of measured data may be stored in the memory in the hand-held instrument for later plotting. Buttons may be provided to store or otherwise access the data in the memory. For example, left and right ear buttons (420 or 422) may be provided. These buttons may be used to direct the null value to a memory location which stores the last peak data for later printing. The ear being tested may be identified as Left or Right on a printed record.

As an additional feature, two sizes of replaceable tips and normalization data may also be provided for selecting the age group being tested. For example, simultaneously pressing the Left and Right ear buttons may be used to cause toggling between Child and Infant tip calibration. Switching to infant operation selects a higher swept frequency range and internal circuit gain while the infant tip adjusts the apparent canal length and modifies the acoustic impedance. Normalization data for the two types of tips may be stored in non-volatile memory, eliminating the need for re-normalization each time the tip is changed. The status of the calibration of the instrument may also be displayed, for example, by displaying a corresponding "C" or "I" on the graphic display and on the plotted curve.

Figures 20C, 20D:
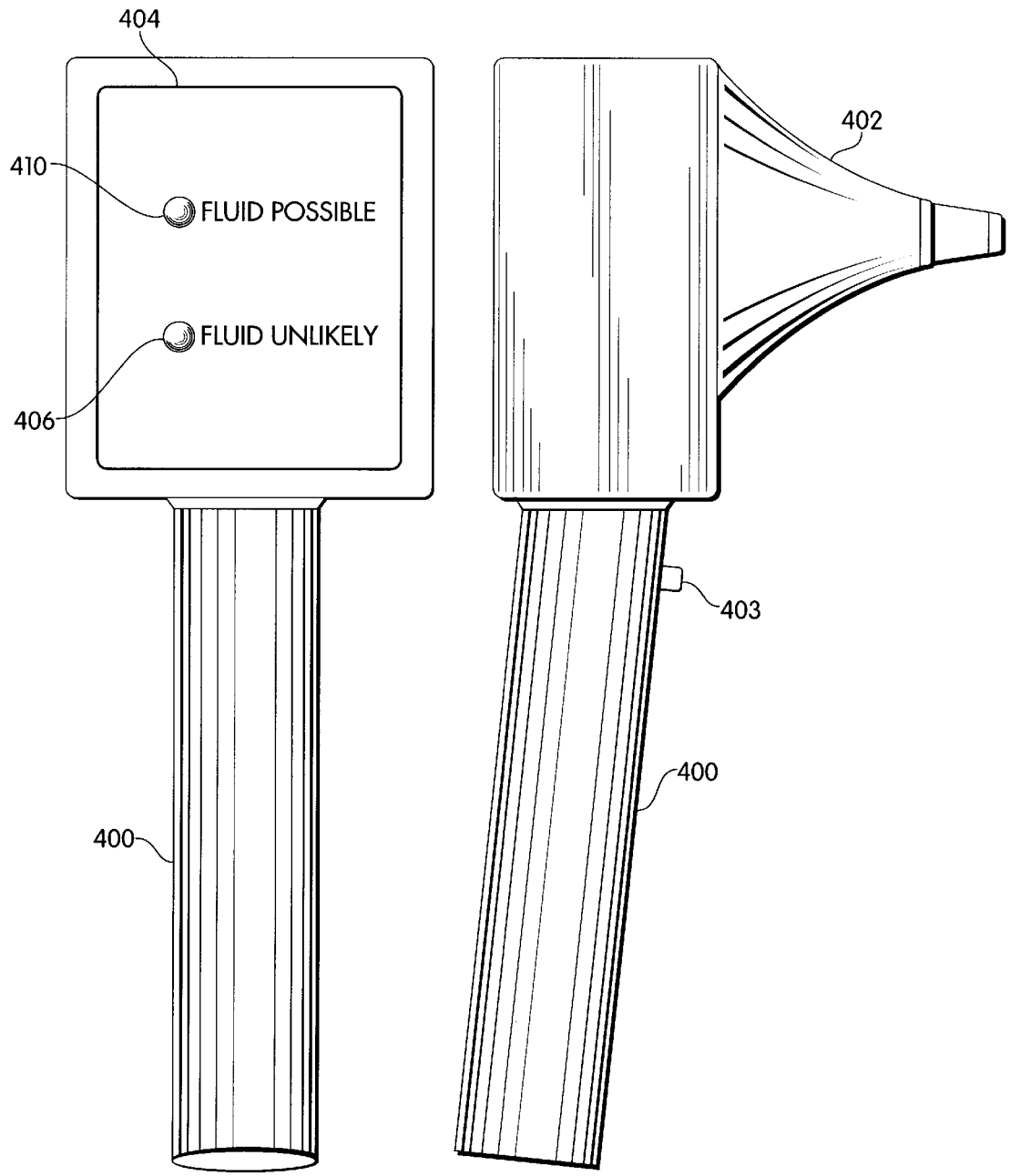
FIGS. 20C and 20D illustrate suitable packaging for a screening instrument in accordance with the present invention.

FIGS. 20c–20d illustrate another embodiment of an instrument in accordance with the invention. Such an instrument could be used for determining when a child should be referred for diagnosis and treatment and also for determining the effectiveness of a treatment regimen. The screening instrument according to the present invention is intended to be a low cost, higher volume screening instrument, for use by non-specialists. The primary use of the screening instrument is likely to be for screening children over six months of age for chronic middle ear effusion (MEE) or abnormal pressure. The device preferably is a low power, stand-alone, battery operated instrument with either replaceable batteries or optional rechargeable batteries. It uses low-power electronic circuitry and power conservation techniques to minimize power consumption. For example, circuits preferably are used only when required and the system automatically enters a stand-by mode when not in use.

In a preferred embodiment, the instrument has a hand piece 400 with replaceable tips 402 that contact the patient. The shape of the hand piece is intended to more closely resemble that of the ubiquitous otoscope. A debounced measure button 403 is pressed by the user to cause a sweep by the oscillator to obtain a measurement.

For purposes of screening the output of such an instrument may be a two light display. The output 404 is displayed as colored lights: a green LED 406 indicates "normal" and a red LED 410 indicates "hearing loss" or other pathology. It may also be desirable to have a screening device with three or more lights as an output. For example, such a device may have lights which are red, referring to a doctor; amber or yellow, suggesting that retesting or continued monitoring be performed; and green, indicating normal hearing. In such a device two thresholds would be used, typically one in the range of 70 to 90 degrees (e.g., 75 degrees) and a second typically in the range of 80 to 100 degrees, e.g., around 95 degrees. The presence of other pathologies can also be indicated using this kind of display. A corrected null value may also be used and compared to thresholds to provide a similar display.

It should be understood that the instruments of FIGS. 20a–20d are exemplary. Other instruments may be made in accordance with the invention and directed to particular users or diagnoses to be provided or suggested.

Having now described a few embodiments of the invention, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention as defined by the appended claims.

What is claimed is:

1. A device for analyzing a human ear, comprising:
    means for directing energy from an energy source into the ear and for detecting reflected energy to produce an electrical signal, wherein the electrical signal has a shape; and
    means for electronically measuring the shape of a region of the electrical signal to obtain an indication of a condition of the ear, wherein the indication is substantially independent of a line of sight from the energy source into the ear.

2. The device of claim 1, wherein the means for directing directs the energy to the tympanic membrane of an ear of an individual.

3. The device of claim 2, wherein the indicated condition of the ear is conductive hearing loss.

4. The device of claim 1, wherein the means for detecting detects a vector sum of reflected energy and energy from the energy source.

5. The device of claim 1, wherein the means for measuring shape includes a means for detecting resonance in the cavity and a frequency at which resonance occurs.

6. A process for analyzing a human ear, comprising:
    directing energy from an energy source into the ear;
    detecting reflected energy to produce an electrical signal, wherein the electrical signal has a shape; and
    electronically measuring the shape of a region of the electrical signal to obtain an indication of a condition of the ear, wherein the indication is substantially independent of a line of sight from the energy source into the ear.

7. The process of claim 6, wherein the step of directing directs the energy to the tympanic membrane of an ear of an individual.

8. The process of claim 7, wherein the indicated condition of the ear is conductive hearing loss.

9. The process of claim 6, wherein the step of detecting includes detecting a vector sum of reflected energy and energy from the energy source.

10. The process of claim 6, wherein the step of measuring shape includes a step of detecting resonance in the cavity and a frequency at which resonance occurs.

11. A device for analyzing a human ear, comprising:
    an energy detector positioned to detect reflected energy from the ear to produce an electrical signal, wherein the electrical signal has a shape; and
    a shape analyzer connected to receive the reflected signal and having an output which provides a measure of the shape of a region of the electrical signal indicative of a condition of the ear, wherein the measure is substantially independent of a line of sight from the device into the ear.

12. The device of claim 11, further comprising an energy source positioned to direct energy into the bodily cavity.

13. The device of claim 12, wherein the bodily cavity is an ear having a tympanic membrane and wherein the indicated condition of the ear is conductive hearing loss.

14. The device of claim 11, wherein the energy detector detects a vector sum of reflected energy and energy from the energy source.

15. The device of claim 11, wherein the shape analyzer detects resonance in the cavity and a frequency at which resonance occurs.

* * * * *